United States Patent
Carswell et al.

(10) Patent No.: US 6,207,656 B1
(45) Date of Patent: *Mar. 27, 2001

(54) VITAMIN D ANALOGUES AND THEIR NEURONAL EFFECTS

(75) Inventors: Susan Carswell, Wallingford; Pawel Dobrzanski, Downingtown, both of PA (US); Lise Binderup, Taastrup (DK); Fredrik Björkling, Helsingborg (SE); Matthew S. Miller, Newtown, PA (US)

(73) Assignees: Cephalon, Inc., West Chester, PA (US); Leo Pharmaceutical Products, Ballerup (DK)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/082,762
(22) Filed: May 21, 1998

Related U.S. Application Data

(60) Provisional application No. 60/047,391, filed on May 22, 1997.
(51) Int. Cl.$^7$ ............... A61K 31/59; A61K 38/18; A61K 38/16
(52) U.S. Cl. ................ 514/167; 514/8; 514/12
(58) Field of Search ................. 514/8, 12, 167

(56) References Cited

U.S. PATENT DOCUMENTS

| | | | |
|---|---|---|---|
| 4,897,388 | 1/1990 | Malluche | 514/167 |
| 5,093,317 | 3/1992 | Lewis et al. | 5514/12 |
| 5,206,229 | 4/1993 | Calverley et al. | 514/167 |
| 5,374,629 | 12/1994 | Calverley et al. | 514/167 |
| 5,420,112 | 5/1995 | Lewis et al. | 514/12 |
| 5,446,034 | 8/1995 | Bretting et al. | 514/167 |
| 5,716,945 | 2/1998 | Grue-Sørensen | 514/167 |
| 5,716,946 | 2/1998 | DeLuca et al. | 514/167 |
| 5,731,284 | * 3/1998 | Williams | 514/8 |
| 5,786,347 | 7/1998 | Hesse et al. | 514/167 |

FOREIGN PATENT DOCUMENTS

| | | |
|---|---|---|
| WO 93/19044 | 9/1993 | (WO). |
| WO 95/02409 | 1/1995 | (WO). |
| WO 95/02577 | 1/1995 | (WO). |

OTHER PUBLICATIONS

Batchelor et al., "Nerve Growth Factor Receptor and Choline Acetyltransferase Colocalization in Neurons Within the Rat Forebrain: Response to Fimbria–Fornix Transection", *J. Comp. Neurol.*, 1989, 284, 187–204.

Binderup et al., "Effects of a Novel Vitamin D Analogue MC 903 On Cell Proliferation and Differentiation In Vitro and on Calcium Metabolism In Vivo", *Biochem. Pharmacol.*, 1988, 37(5), 889–895.

Crook et al., "Age–Associated Memory Impairment: Proposed Diagnostic Criteria and Measures of Clinical Change—Report of a National Institute of Mental Health Work Group", *Devel. Neuropsych.*, 1986, 2(4), 261–276.

Evans et al., "Prevalence of Alzheimer's Disease in a Community Population of Older Persons", *JAMA*, 1989, 262(18), 2551–2556.

Jehan et al., "MC903, an analogue of 1,25–dihydroxyvitamin D3, increases the synthesis of nerve growth factor", *Eur. J. Pharm—Mol. Pharm. Section.*, 1991, 208, 189–191.

Katzman et al., "Advances in Alzheimer's Disease", *FASEB J.*, 1991, 5, 278–286.

Kotzbauer et al., "Neurturin, a relative of glial–cell–line–derived neurotrophic factor", *Nature*, 384, 467–470 (Dec. 1996).

Lapchak et al., "Therapeutic Potential for Nerve Growth Factor In Alzheimer's Disease: Insights from Pharmacological Studies Using Lesioned Central Cholinergic Neurons", *Rev. Neurosciences*, 1992, 3(2), 109–119.

Lemire et al., "1,25–Dihydroxyvitamin $D_3$ Prevents the In Vivo Induction of Murine Experimental Autoimmune Encephalomyelitis", *J. Clin. Invest.*, 1991, 87, 1103–1107.

Matsuyama et al., "Senile Changes in the Brain in the Japanese. Incidence of Alzheimer's Neurofibrillary Change and Senile Plaques", Proceedings of the Fifth International Congress of Neuropathy, Exerpta Medica International Congress Series No. 100, Luthy et al. (eds.), 1966, 979–980.

Srebro et al., "Changes in Acetylcholinesterase Activity in Hippocampus Produced by Septal Lesions in the Rat", *Life Sci.*, 1972, 12(1), 261–270.

Williams et al., "Glial Cell Line–Derived Neurotropic Factor Sustains Axotomized Basal Forebrain Cholinergic Neurons In Vivo: Dose–Response Comparison to Nerve Growth Factor and Brain–Derived Neurotrophic Factor", *J. Pharm. Exp. Therap.*, 1996, 277(2), 1140–1151.

Wion et al., "1,25–Dihydroxyvitamin $D_3$ Is a Potent Inducer of Nerve Growth Factor Synthesis", *J. Neurosciences Res.*, 1991, 28, 110–114.

* cited by examiner

Primary Examiner—Ardin H. Marschel
Assistant Examiner—Marjorie A. Moran
(74) Attorney, Agent, or Firm—Fish & Richardson P.C.

(57) ABSTRACT

The present invention is directed, inter alia, to methods of utilizing low calcemic vitamin D analogues. Particularly, the present invention is directed to using low calcemic vitamin D analogues to treat neurodegenerative diseases and disorders, to facilitate endogenous production of neurotrophic factors, to inhibit the degradation, dysfunction or loss of neural cells and/or to enhance the phenotype of neural cells or neuronal processes.

52 Claims, 17 Drawing Sheets

*p<0.05 vs. VEHICLE TREATED (1 TAILED TEST)

** $p<.01$ vs. SHAM, ¶ $p<.05$ vs. VEHICLE

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 18 bases
      (B) TYPE: nucleic acid
      (C) STRANDEDNESS: single
      (D) TOPOLOGY: linear (xi) SEQUENCE DESCRIPTION: SEQ ID NO:1:

CTAAACTTCA GCATTCCC  18

(2) INFORMATION FOR SEQ ID NO:2:

(i) SEQUENCE CHARACTERISTICS:
      (A) LENGTH: 18 bases
      (B) TYPE: nucleic acid
      (C) STRANDEDNESS: single
      (D) TOPOLOGY: linear (xi) SEQUENCE DESCRIPTION: SEQ ID NO:2:

AAAGGTGTGA GTCGTGGT  18

(2) INFORMATION FOR SEQ ID NO:3:

(i) SEQUENCE CHARACTERISTICS:
      (A) LENGTH: 24 bases
      (B) TYPE: nucleic acid
      (C) STRANDEDNESS: single
      (D) TOPOLOGY: linear (xi) SEQUENCE DESCRIPTION: SEQ ID NO:3:

GTGGAGCTTC GAGAACTTTC TCCC  24

(2) INFORMATION FOR SEQ ID NO:4:

(i) SEQUENCE CHARACTERISTICS:
      (A) LENGTH: 30 bases
      (B) TYPE: nucleic acid
      (C) STRANDEDNESS: single
      (D) TOPOLOGY: linear (xi) SEQUENCE DESCRIPTION: SEQ ID NO:4:

TAGCGGATGT GTACGTCCAG GAAGGACACC  30

(2) INFORMATION FOR SEQ ID NO:5:

(i) SEQUENCE CHARACTERISTICS:
      (A) LENGTH: 23 bases
      (B) TYPE: nucleic acid (C) STRANDEDNESS: single
        (D) TOPOLOGY: linear (xi) SEQUENCE DESCRIPTION: SEQ ID NO:5:

GAAGTTATGG GATGTCGTGG CTG                                              23

(2) INFORMATION FOR SEQ ID NO:6:

(i) SEQUENCE CHARACTERISTICS:
        (A) LENGTH: 22 bases
        (B) TYPE: nucleic acid
        (C) STRANDEDNESS: single
        (D) TOPOLOGY: linear (xi) SEQUENCE DESCRIPTION: SEQ ID NO:6:

TCTGGCCTCT GCGACCTTTC CC                                               22

(2) INFORMATION FOR SEQ ID NO:7:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:7:

GCTGAGTGAC AGCACCCCTT                                                  20

(2) INFORMATION FOR SEQ ID NO:8:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:8:

GCGCCAGCCT ACGAGTTTGT                                                  20

(2) INFORMATION FOR SEQ ID NO:9:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:9:

GCAAACATGT CTATGAGGGT                                                  20

(2) INFORMATION FOR SEQ ID NO:10:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:10:

GGTCAGTGTA CATACACAGG                                                  20

(2) INFORMATION FOR SEQ ID NO:11:

(i) SEQUENCE CHARACTERISTICS:
        (A) LENGTH: 21 bases
        (B) TYPE: nucleic acid
        (C) STRANDEDNESS: single

```
            (D) TOPOLOGY: linear (xi) SEQUENCE DESCRIPTION: SEQ ID NO:11:

TGGCTAGCAA GGAAGATTCG T                                    21

(2) INFORMATION FOR SEQ ID NO:12:

(i) SEQUENCE CHARACTERISTICS:
            (A) LENGTH: 21 bases
            (B) TYPE: nucleic acid
            (C) STRANDEDNESS: single
            (D) TOPOLOGY: linear (xi) SEQUENCE DESCRIPTION: SEQ ID NO:12:

ACGAAGGTCA TGGATGGACC T                                    21
```

VITAMIN D ANALOGUES AND THEIR NEURONAL EFFECTS

CROSS-REFERENCE TO RELATED APPLICATIONS

This application claims the benefit of U.S. Provisional Application No. 60/047,391, filed May 22, 1997.

FIELD OF THE INVENTION

The present invention is directed to the use of vitamin D analogues to mediate neuronal effects.

BACKGROUND OF THE INVENTION

Diseases associated with the loss of neurons in different regions of the central nervous system (CNS), including, for example, brain tissue and the spinal cord, are the subject of intense research. Exemplary diseases are Alzheimer's disease, amyotrophic lateral sclerosis ("ALS" or "Lou Gehrig's disease"), Parkinson's disease, Huntington's disease, ischaemia, and stroke. These types of diseases are exemplary of diseases and disorders collectively referred to herein as "neurodegenerative diseases." The incidence of many neurodegenerative diseases increases rapidly with aging. For example, less than 5% of the population under the age of 65 have Alzheimer's disease. This incidence increases almost exponentially over the age of 65, and as much as 47% of the population over the age of 85 have some form of Alzheimer's disease. See, Katzman et al, *FASEB*, 5:278–286 (1991); Evans et al, *JAMA*, 262:2551–2556 (1989). A study of individuals over the age of 80 revealed that the brains of substantially all the individuals studied contained at least some age- and/or disease-related loss of neurons. See, Matsuyama et al, *Proceedings of the Fifth International Congress of Neuropathy*, (Exerpta Medica International Congress Series No. 100 eds. Luthy et al) 979–980 (1966). These studies indicate that aging is a major risk factor for the development of neurodegenerative diseases. In fact, there is evidence suggesting that even in the absence of disease, the aging process is associated with neuron loss and memory impairment. Crook et al, *Devel. Neuropsych.*, 2(4):261–276 (1986).

The causes of neurodegenerative diseases and the associated loss of neurons, as well as neuron loss associated with aging, remains unclear. It has been proposed that neurodegenerative diseases and the associated loss of neurons may be treated by administering the protein nerve growth factor (NGF). See, Lapchak et al, *Reviews in the Neurosciences*, 3:109–119 (1992). NGF is required for the maintenance and survival of sympatic and sensory neurons in the peripheral nervous system, as well as for basal forebrain cholinergic neurons in the central nervous system. See, Lapchak et al, *Reviews in the Neurosciences*, supra.

However, exogenous administration of NGF as a putative therapeutic for neurodegenerative diseases of the CNS is not practical because NGF is unable to cross the blood-brain barrier. Methods for increasing endogenous NGF levels by administering 1,25-dihydroxy vitamin $D_3$ or an analogue thereof have been proposed as a therapeutic approach. See, Jehan et al, *EJPMOL*, 208:189–191 (1991); Wion et al, *J. Neurosciences Res.*, 28:110–114 (1991). Similarly, U.S. Pat. No. 4,897,388 describes a method for treating Alzheimer's disease using calcitriol and analogues thereof, while PCT Application PCT/US94/07917 describes methods for protecting against neuron loss using calcitriol and analogues thereof. However, 1,25-dihydroxy vitamin $D_3$ and many of its analogues increase serum calcium levels at doses that induce NGF. The hypercalcemia elicited by 1,25-dihydroxy vitamin $D_3$ and many of its analogues leads to wasting, depletion of calcium from bone, and calcification of soft tissues, making these compounds poor therapeutic candidates.

It has also been proposed that neurodegenerative diseases and the associated loss of neurons may be treated by administering or over-expressing other neurotrophic factors, e.g., insulin-like growth factor (IGF), glial cell line-derived neurotrophic factor (GDNF), neurturin, or brain-derived neurotrophic factor (BDNF). See, U.S. Pat. No. 5,093,317; Williams et al, *JPET*, 277(2):1140–1151 (1996); Kotzbauer et al, *Nature*, 384–467–470 (1996). GDNF has been found to stimulate and prevent the loss of mesencephalic dopaminergic neurons, somatic motor neurons and basal forebrain cholinergic neurons. See, Williams et al, *JPET*, supra. Neurturin was recently discovered and has been found to stimulate and prevent the loss of sympathetic and sensory neurons in the peripheral nervous system (PNS). These are the neurons in the PNS that NGF act upon. The activity profile of neurturin in the CNS has not yet been publicly described. Along with NGF, BDNF and neurotrophin 3 (NT-3) are members of a family of trophic factors known as "neurotrophins." BDNF has been found to prevent the loss of basal forebrain cholinergic cells, as well as several other neuronal cell types. See, Williams et al, *JPET*, supra. NT-3 has been found to prevent the loss of multiple neuronal cell types, including sympatic and sensory neurons in the PNS.

As discussed above, exogenous administration of GDNF, neurturin, NT-3, and/or BDNF as a putative therapeutic for neurodegenerative diseases is not practical because these neurotrophic factors are generally unable to cross the blood-brain barrier. Thus, increasing endogenous levels of these neurotrophic factors by peripherally administering small molecules which can cross the blood-brain barrier is an important therapeutic approach.

Another type of disease affecting neurons is multiple sclerosis. Multiple sclerosis is thought to result from central nervous system demyelination brought about by chronic inflammatory autoimmune reaction. It has been proposed to treat multiple sclerosis by the administration of vitamin D. For example U.S. Pat. No. 5,716,946 to DeLuca discloses the use of 1,25-dihydroxy vitamin $D_3$ or analogs thereof to treat multiple sclerosis. However, as discussed previously 1,25-dihydroxy vitamin $D_3$ and many of its analogues undesirably increase serum calcium levels at doses useful for treating multiple sclerosis.

Therefore, it is an object of the present invention to provide a method of treating neurodegenerative diseases or multiple sclerosis using low calcemic vitamin D analogues. It is another object of the present invention to provide a method for facilitating the production of neurotrophic factors or inhibiting the degradation or loss of neural cells.

SUMMARY OF THE INVENTION

The present invention is directed, inter alia, to methods of using low calcemic vitamin D analogues for treating neurodegenerative diseases, for facilitating the endogenous production of neurotrophic factors, such as GDNF, CTNF, NGF, NRT, NT-3 and BDNF, for inhibiting the degradation, dysfunction, or loss of neural cells, or enhancing the phenotype of neural cells or neuronal processes.

The vitamin D analogues that are useful in the present invention include compounds of Formula I:

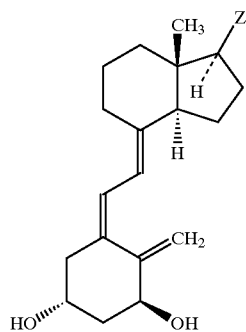

(I)

wherein Z is selected from the group consisting of

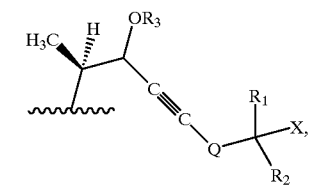

(Y$_1$)

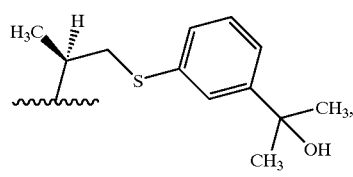

(Y$_2$)

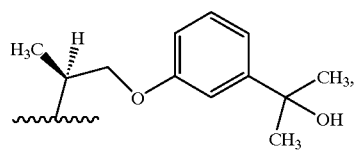

(Y$_3$)

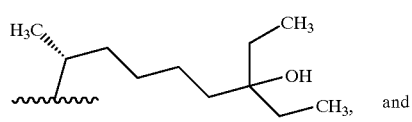

(Y$_4$) and

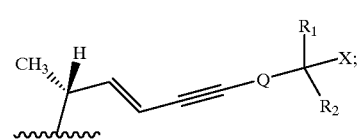

(Y$_5$)

and wherein

X is a hydrogen atom or a hydroxy group;

$R_1$ and $R_2$ each independently represent a hydrogen atom or a $C_1$–$C_6$ alkyl group that is optionally substituted with one or more deuterium or fluorine atoms, or $R_1$ and $R_2$, taken together with the carbon atom bearing the X group, form a $C_3$–$C_8$ cyclic ring that is optionally substituted with one or more deuterium or fluorine atoms;

$R_3$ is a hydrogen atom, a $C_1$–$C_{10}$ alkyl group that is optionally substituted with one or more deuterium or fluorine atoms or $YR_4$, wherein Y is —CO—, —COO—, —COS—, —CS—, —CSO—, —CSS—, —SO— or —SO$_2$— and $R_4$ is a hydrogen atom or a $C_1$–$C_{10}$ alkyl group that is optionally substituted with one or more deuterium or fluorine atoms; and Q is a single bond or a $C_1$–$C_8$ alkylene group that is optionally substituted with one or more deuterium or fluorine atoms.

Preferred compounds of Formula (I) include Compound (A), when Z is Y$_1$, Compound (B), when Z is Y$_2$; Compound (C), when Z is Y$_3$; Compound (D), when Z is Y$_4$, or Compound (E), when Z is Y$_5$:

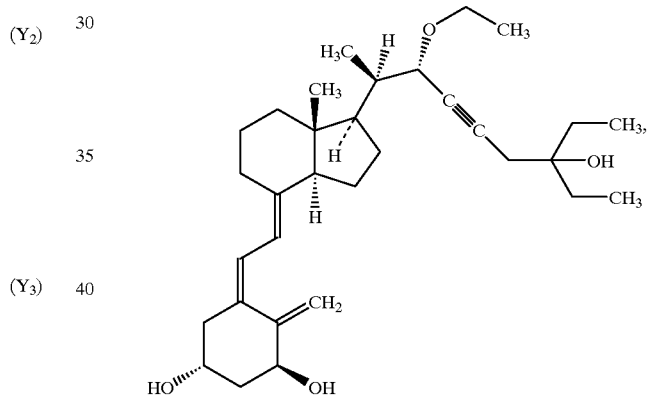

(A)

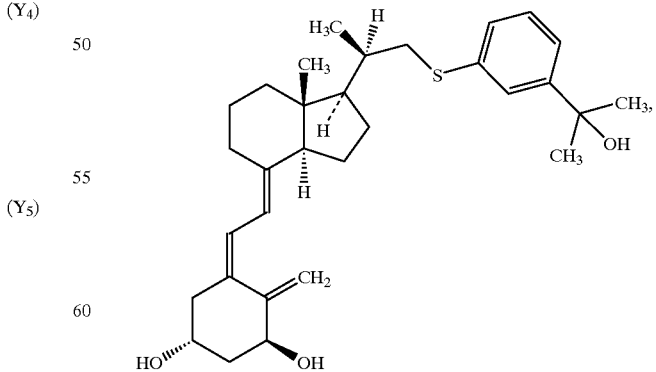

(B)

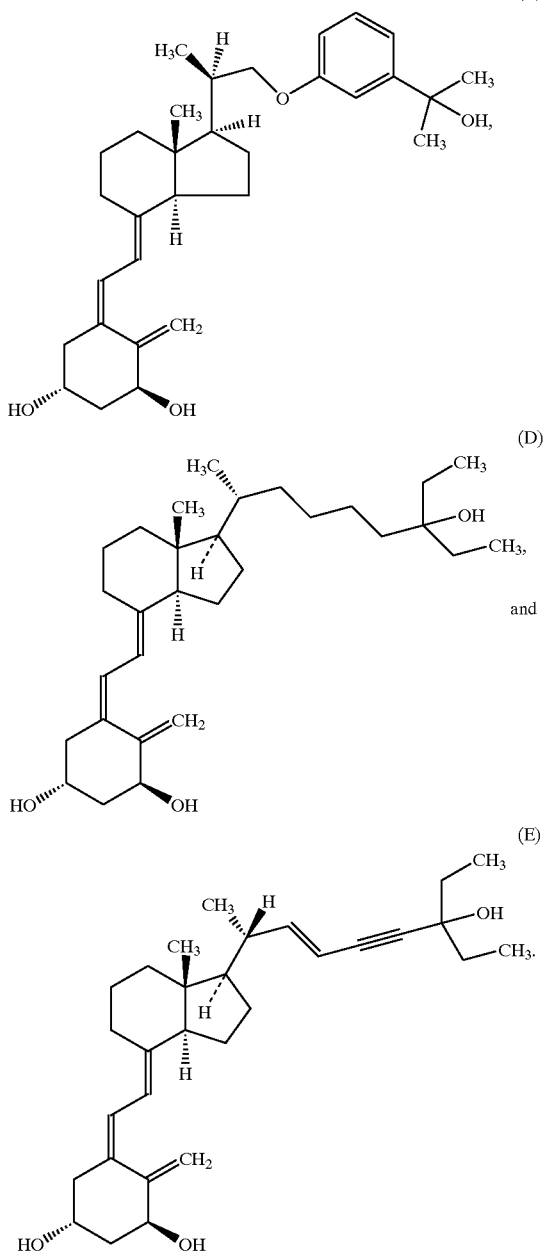

In another embodiment of the present invention, the compounds of Formula (I) may be administered to treat peripheral neuropathy or to treat multiple sclerosis.

Additionally, the low calcemic vitamin D analogues, including, for example, the compounds of Formula (I), may be used in the manufacture of a medicament for the prevention and/or treatment of neurodegenerative diseases, including, for example, Alzheimer's disease, amyotrophic lateral sclerosis ("ALS" or "Lou Gehrig's disease"), Parkinson's disease, Huntington's disease, ischaemia, stroke, aging, and peripheral neuropathy. The low calcemic vitamin D analogues useful in the present invention may also be used in the manufacture of a medicament for the treatment of multiple sclerosis.

These and other aspects of the invention will be elucidated in detail below.

BRIEF DESCRIPTION OF THE FIGURES

FIG. 11A shows the time course with the dose response;

FIG. 11B shows the average landing foot spread for days 1–42; and

FIG. 11C shows the average landing foot spread for (days 1–24 and days 24–42.

FIG. 12A shows the total dose response with the time course, and FIG. 12B shows the results on days 33, 37 and 40.

FIG. 13A shows the total dose response with the time course, and FIG. 13B shows the results on day 40.

DETAILED DESCRIPTION OF THE INVENTION

Figure 1:
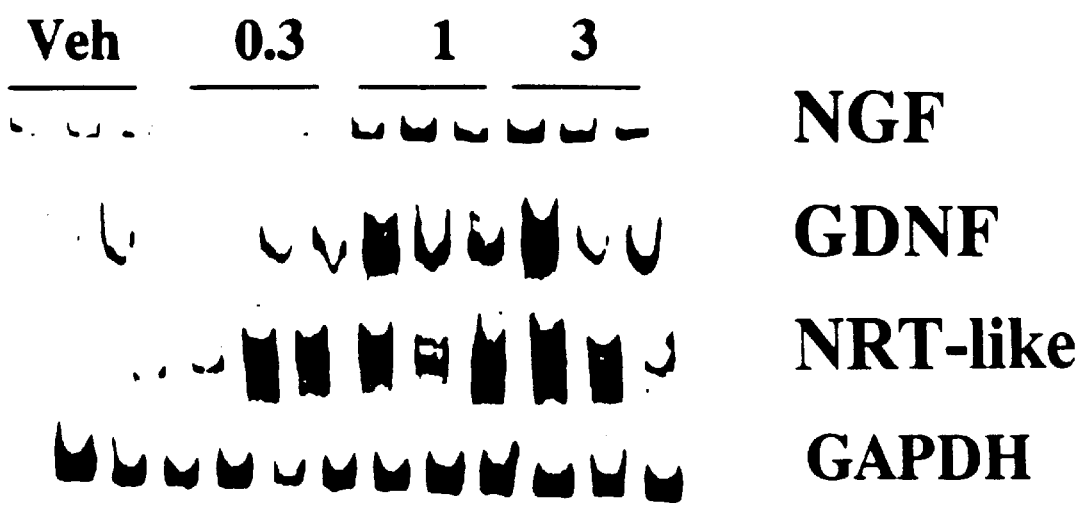
FIG. 1 is a computer generated reverse transcriptase polymerase chain reaction analyses showing the expression of NGF, GDNF, BDNF, NRT-like, NT-3 and GAPDH mRNA utilizing various amounts of Compound (A) of the present invention.
Figure 1:
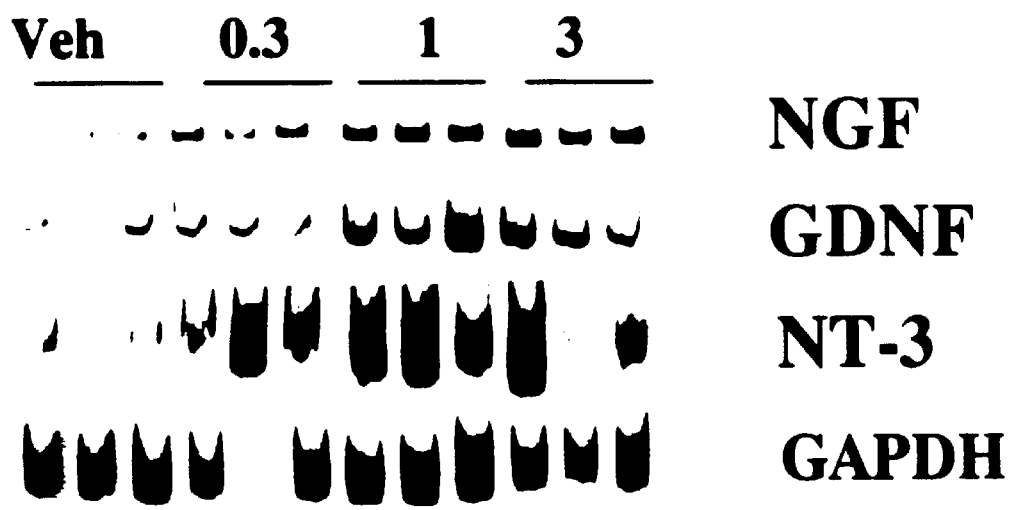
Figure 1:
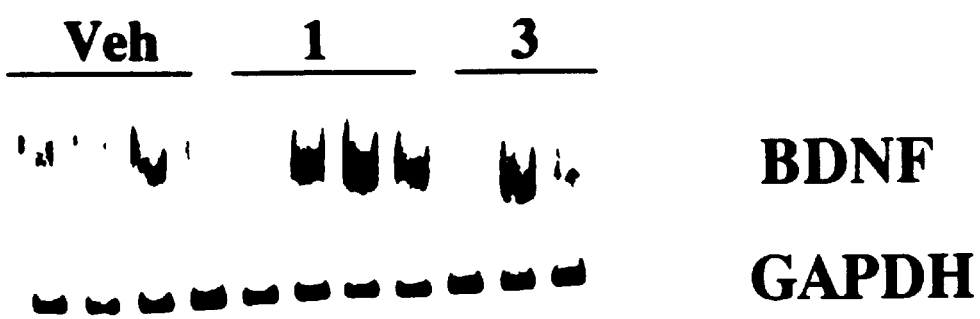

As employed throughout the disclosure, the following terms, unless otherwise indicated, shall be understood to have the following meanings.

Throughout the disclosure, the following abbreviations are employed: IGF, insulin-like growth factor; NGF, nerve growth factor; GDNF, glial cell line-derived neurotrophic factor; BDNF, brain-derived neurotrophic factor; NRT, neurturin or a neurturin-like substance; NT-3, neurotrophin 3; CTNF, ciliary neurotrophic factor; ChAT, choline acetyltransferase; CNS, central nervous system; PNS, peripheral nervous system; and GAPDH, glyceraldehyde-3-phosphate dehydrogenase. By "neurturin-like" it is meant any gene containing a sequence recognized by the NRT-like primer in Example 3.

"Low calcemic vitamin D analogues" refer to analogues of 1,25-dihydroxy vitamin $D_3$ that, when administered to a mammal, produce no or substantially no increase in serum calcium levels of such mammal at doses where 1,25-dihydroxy vitamin $D_3$ does increase such serum calcium levels. A generally accepted laboratory reference range for serum calcium levels in an otherwise normal, healthy human is between about 8.4 and about 10.5 mg calcium/dL serum or between about 2.1 and about 2.6 mmol calcium/L serum. The phrase "substantially no increase in serum calcium levels" means an increase in calcium levels of less than about 25% of control calcium levels, preferably an increase in calcium levels of less than about 20%, more preferably less than about 15%, and most preferably less than about 10% of such levels. Thus, a preferred value for substantially no increase in homeostatic, endogenous calcium levels in humans would be less than about 12.6 mg/dL.

"Neuron" or "neural cell" refers to any of the conducting cells of the central, peripheral or autonomic nervous systems which generally comprise a cell body containing the nucleus and the surrounding cytoplasm (perikaryon), several short radiating processes (dendrites), and one long process (axon), which terminates in twig-like branches (telodendrons) and which may have branches (collaterals) projecting along its course. Neural cells include, by way of example and not limitation, cholinergic neural cells, glutamatergic neural cells, dopaminergie neural cells, motor neural cells, sympatic neural cells and sensory neural cells.

"Degradation," "dysfunction" or "loss" of neural cells refers to the weakening, lessening and/or destruction of neurons or an anatomical component of neurons, including but not limited to dendrites, axons, telodendrons or collaterals (i.e., "neuronal processes") and/or neuronal processes. The degradation, dysfunction or loss of neurons is generally associated with neurodegenerative diseases, including, for example, Alzheimer's disease, amyotrophic lateral sclerosis ("ALS" or "Lou Gehrig's disease"), Parkinson's disease, Huntington's disease, ischaemia, and stroke, as well as aging, generally. The term "neurodegenerative diseases" as used herein is not meant to include multiple sclerosis.

"Inhibiting the degradation, dysfunction or loss, and/or enhancing the phenotype, of neural cells and/or neuronal processes" refers to any means of inhibiting the weakening, lessening and/or destruction of neurons, and may include, for example, strengthening weakened or damaged neurons and/or increasing the number of functioning neurons in the nervous system and/or enhancing the survival of a neural cell at risk of dying. By way of example, a compound is said to inhibit degradation, dysfunction or loss, and/or enhance the phenotype, of neural cells if, e.g., in a comparative sense, neural cells that are otherwise at risk of dying (due to, e.g., a disease or experimental condition) are exposed to the compound whereby a significant percentage of such at risk cells do not otherwise degrade. In vivo, a compound is said to inhibit the degradation or loss of neural cells if, e.g., a biological and/or behavioral aspect associated with such cells, which aspect would otherwise be expected to deteriorate due to, e.g., a disease, does not deteriorate (or deteriorates with less rapidity) after administration of such compound.

"Compounds that facilitate the endogenous production of neurotrophic factors" refers to compounds that express neurotrophic factors, up-regulate neurotrophic factors or cause the number of endogenous neurotrophic factors in the nervous system to increase by any means. Although not intending to be bound by any theory of the invention, it is believed that increasing the number of endogenous neurotrophie factors in the central nervous system increases the number of neurotrophic factors that positively impact neural cells. As used in this definition, a "neurotrophic factor" is most preferably a protein which inhibits the degradation or loss of neural cells or increases the function (e.g., enhances the phenotype) of neural cells. Exemplary neurotrophic factors include, by way of example but not limitation, GDNF, BDNF, NRT (including neurturin-like), NT-3, CTNF, NGF, IGF-1, or combinations thereof. Preferably, the compounds useful in the present invention facilitate the production of GDNF, BDNF, NT-3, NGF or combinations thereof. In another preferred embodiment the compounds useful in the present invention facilitate the production of GDNF, BDNF, or NT-3, where NGF is not expressed. For purposes of this disclosure, a compound that facilitates the production of a neurotrophic factor in vitro, coupled with evidence that such neurotrophic factor inhibits the degradation or loss of neural cells, is by definition herein a compound which is Liseful in the treatment of neurodegenerative diseases and disorders as detailed below. Such compounds, for purposes of this disclosure, are low calcemic vitamin D analogues as detailed herein.

"About" in reference to a numerical value means +/−10% of the value, e.g., "about 10%" means approximately 9–11%.

"Patient" refers to animals, preferably mammals, more preferably humans.

"Alkyl" refers to an aliphatic hydrocarbon group which may be straight, branched or cyclic having 1 to about 60 carbon atoms in the chain. "Lower alkyl" refers to an alkyl group having 1 to about 5 carbon atoms. The alkyl group may be optionally substituted with one or more alkyl group substituents which may be the same or different, where "alkyl group substituent" includes halo, aryl, hydroxy, alkoxy, aryloxy, alkyloxy, alkylthio, arylthio, aralkyloxy, aralkylthio, carboxy alkoxycarbonyl, oxo and cycloalkyl. There may be optionally inserted along the alkyl group one or more oxygen, sulphur or substituted or unsubstituted nitrogen atoms, wherein the nitrogen substituent is lower alkyl. "Branched" refers to an alkyl group in which a lower alkyl group, such as methyl, ethyl or propyl, is attached to a linear alkyl chain. Exemplary alkyl groups include methyl, ethyl, i-propyl, n-butyl, t-butyl, n-pentyl, heptyl, octyl, decyl, dodecyl, tridecyl, tetradecyl, pentadecyl and hexadecyl. Preferred alkyl groups include the lower alkyl groups of 1 to about 5 carbon atoms.

"Cycloalkyl" refers to a non-aromatic mono- or multicyclic ring system of about 3 to about 10 carbon atoms. The cycloalkyl group may be optionally partially unsaturated. The cycloalkyl group may be also optionally substituted with an aryl group substituent, oxo and/or alkylene. "Lower cycloalkyl" refers to a monocyclic ring system of about 3 to about 7 carbon atoms. Preferred cycloalkyl rings include cyclopentyl, cyclohexyl and cycloheptyl.

"Alkylene" refers to a straight or branched bivalent aliphatic hydrocarbon group having from 1 to about 30 carbon atoms. The alkylene group may be straight, branched or cyclic. The alkylene group may be also optionally unsaturated and/or substituted with one or more "alkyl group substituents." There may be optionally inserted along the alkylene group one or more oxygen, sulphur or substituted or unsubstituted nitrogen atoms, wherein the nitrogen substituent is alkyl as previously described. Exemplary alkylene groups include methylene (—CH$_2$—), ethylene (—CH$_2$CH$_2$—), propylene (—(CH$_2$)$_3$—), cyclohexylene (—C$_6$H$_{10}$—), —CH=CH—CH=CH—, —CH=CH—CH$_2$—, methylenedioxy (—O—CH$_2$—O—) and ethylenedioxy (—O—(CH$_2$)$_2$—O—). It is preferred that the alkylene group has 2–3 carbon atoms.

"Pharmaceutically acceptable salt" refers to an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine.

The present invention is directed to, among other things, the unexpected discoveries that certain low calcemic vitamin D analogues can be used in the treatment of neurodegenerative diseases, can facilitate the endogenous production of neurotrophic factors, such as GDNF, NT-3, NRT (including neurturin-like), CTNF, NGF, BDNF, or combinations thereof and can inhibit the degradation, dysfunction or loss of neural cells and/or neuronal processes.

Vitamin D analogues which may be used in the present invention include the compounds described by Bretting et al, U.S. Pat. No. 5,446,034; PCT Application WO 93/19044; Grue-Sorensen, U.S. Pat. No. 5,716,945; and EP 0708755; the disclosures of each of which are hereby incorporated by reference herein in their entirety. Additionally, vitamin D analogues in the genera described by Calverley et al, U.S. Pat. No. 5,374,629 and Calverley et al, U.S. Pat. No. 5,206,229, the disclosures of each of which are hereby incorporated by reference herein in their entirety, are amenable to utilization in the present invention.

The compounds which may be utilized in accordance with the present invention may be represented by the Formula (I):

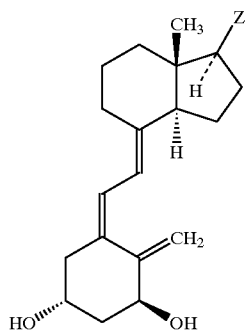

(I)

wherein Z may be $Y_1$, $Y_2$, $Y_3$, $Y_4$, or $Y_5$ as follows:

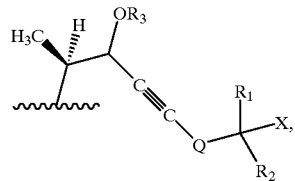

(Y$_1$)

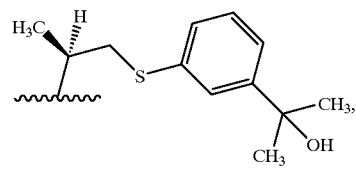

(Y$_2$)

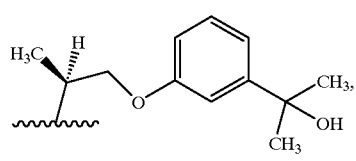

(Y$_3$)

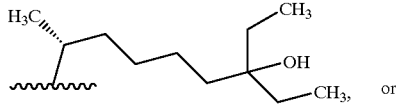

(Y$_4$)

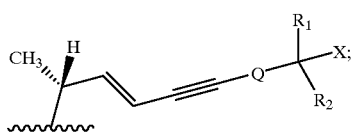

(Y$_5$)

and wherein

X is a hydrogen atom or a hydroxy group;

R$_1$ and R$_2$ each independently represent a hydrogen atom or a C$_1$–C$_6$ alkyl group that is optionally substituted with one or more deuterium atoms or fluorine atoms, or R$_1$ and R$_2$, taken together with the carbon atom bearing the X group, form a C$_3$–C$_8$ cycloalkyl ring that is optionally substituted with one or more deuterium atoms or fluorine atoms;

R$_3$ is a hydrogen atom, a C$_1$–C$_{10}$ alkyl group that is optionally substituted with one or more deuterium atoms or fluorine atoms or YR$_4$; wherein Y is —CO—, —COO—, —COS—, —CS—, —CSO—, —CSS—, —SO— or —SO$_2$—, and R$_4$ is a hydrogen atom or a C$_1$–C$_{10}$ alkyl group that is optionally substituted with one or more deuterium atoms or fluorine atoms; and Q is a single bond or a C$_1$–C$_8$ alkylene group that is optionally substituted with one or more deuterium atoms or fluorine atoms.

Examples of R$_1$ and R$_2$, which may be the same or different, include hydrogen, a methyl group, a trifluoromethyl group, an ethyl group, a vinyl group, a n-propyl group, an isopropyl group, a cyclopropyl group and a 1-methylvinyl group. R$_1$ and R$_2$ when taken together with the carbon atom bearing the X group, may be dimethylene, trimethylene, tetramethylene and pentamethylene. Preferably R$_1$ and R$_2$ are each independently a C$_1$ to C$_4$ alkyl group, more preferably a C$_1$ to C$_3$ alkyl group.

As shown in the Formulas Y$_1$, Y$_2$, Y$_3$, Y$_4$ and Y$_5$, the "⁓" denotes the point of attachment to Formula I. Additionally where it is described that deuterium atoms or fluorine atoms may be substituted, it is meant herein that one or more hydrogens on an alkyl group are replaced with deuterium atoms or fluorine atoms.

Examples of $R_3$ and $R_4$, which may be the same or different, include a hydrogen atom, a methyl group, a trifluoromethyl group, an ethyl group, a propyl group, a n-propyl group, an isopropyl group, a cyclopropyl group, a n-butyl group, an isobutyl group, a sec-butyl group, a t-butyl group, a n-pentyl group, an isopentyl group, a phenyl group and a benzyl group. Preferably, $R_3$ is a $C_1$ to $C_{10}$ alkyl group, more preferably a $C_1$ to $C_6$ alkyl group, even more preferably a $C_1$ to $C_3$ alkyl group.

Examples of Q include a single bond, a methylene group, a dimethylene group, a trimethylene group, a tetramethylene group, $-CH_2-CH=CH-$, $-CH_2-C\equiv C-$, $-CH=CH-CH_2-$, $-C\equiv C-CH_2-$, a phenylene group (ortho, meta, para), $-CH_2-(C_6H_4)-$(ortho, meta, para) and $(C_6H_4)-CH_2-$(ortho, meta, para). Preferably, Q is a $C_1$ to $C_5$ alkylene group, more preferably a $C_1$ to $C_4$ alkylene group, even more preferably a $C_1$ to $C_3$ alkylene group.

Depending on the selection of the $R_1$, $R_2$, $R_3$, Q and X substituents, the compounds of Formula (I) can comprise several diastereoisomeric forms. For example, the compounds which may be utilized in accordance with the present invention may contain at least one asymmetric carbon atom. Accordingly, the compounds can exist as a mixture of enantiomers or as pure enantiomers. In addition, the compounds which may be utilized in accordance with the present invention may contain two or more asymmetric carbon atoms. These compounds can exist as racemic mixtures, diastereoisomeric mixtures or as individual enantiomers. For example, in the compound of Formula (I), when Z is $Y_1$ or $Y_5$, the carbon atoms located between the 5-carbon cyclic ring structure and the $C\equiv C$ bond may comprise several diastereoisomeric forms. Similarly, the carbon atom attached to the Q, X, $R_1$ and $R_2$ substituents in Formula (I) when Z is $Y_1$ or $Y_5$ may comprise several diastereoisomeric forms. The methods of the present invention cover all of the isomers in pure form and also as mixtures.

In a preferred embodiment, when Z is $Y_1$ the compound of Formula (I) is 1(S),3(R)-dihydroxy-20(R)-(1-ethoxy-5-ethyl-5-hydroxy-2-heptyn-1-yl)-9,10-seco-pregna-5(Z),7(E),10(19)-triene, isomer A (hereafter "Compound (A)"). A method of making Compound (A) is disclosed in Example 9 of U.S. Pat. No. 5,446,034. The chemical structure of Compound (A) is as follows:

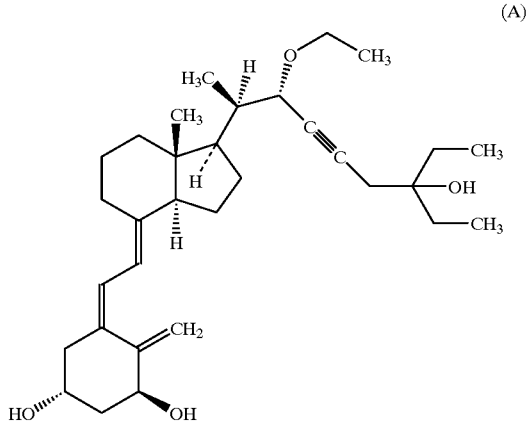

(A)

Other preferred low calcemic vitamin D analogues useful in the present invention are when Z is $Y_2$, $Y_3$, or $Y_4$ in the compound of Formula I. For example, when Z is $Y_2$, the compound of Formula I is 1(S),3(R)-dihydroxy-20(R)-(3-((1-hydroxy-1-methyl)ethyl)phenylthiomethyl)-9,10-seco-pregna-5(Z),7(E),10(19)-triene (hereafter "Compound (B)"). When Z is $Y_3$, the compound of Formula I is 1(S), 3(R)-dihydroxy-20(R)-[3-(2-hydroxy-2-propyl)-phenoxymethyl]-9,10-seco-pregna-5(Z),7(E),10(19)-triene (hereafter "Compound (C)"). When Z is $Y_4$, the compound of Formula I is hereafter referred to as "Compound (D)." For suitable methods of preparing Compounds (B), (C), and (D) see for example, Example 22 of U.S. Pat. No. 5,374,629 for Compound (B); Example 10 of U.S. Pat. No. 5,374,629 for Compound (C); and U.S. Pat. No. 5,206,229 for Compound (D); the disclosures of which are hereby incorporated by reference herein in their entireties. The chemical structures of Compounds (B), (C), and (D) are the following:

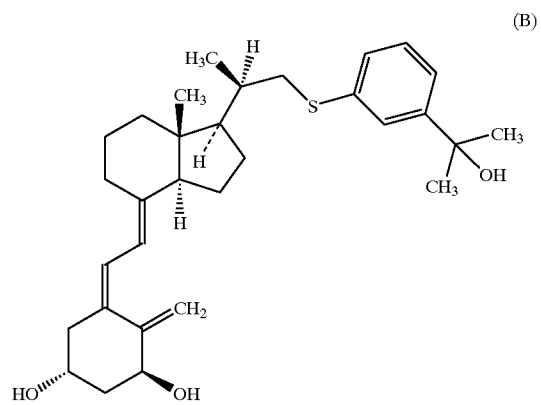

(B)

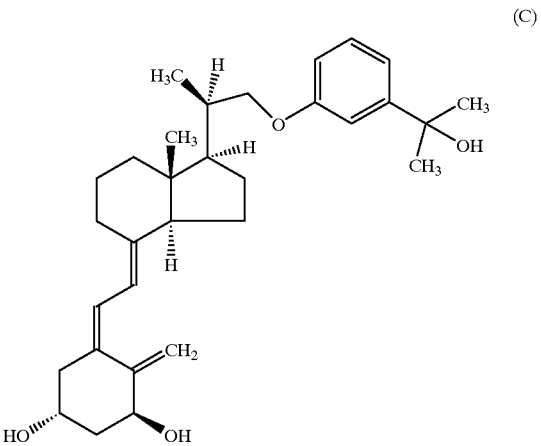

(C)

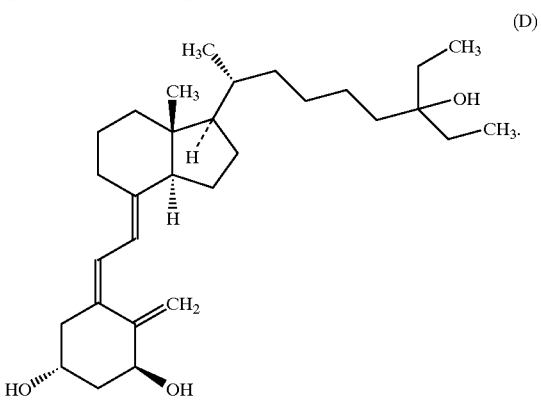

(D)

In yet another preferred embodiment, when Z is $Y_5$, the low calcemic vitamin D analogue useful in the present invention is 1(S)-,3-(R)-Dihydroxy-20(R)-(5-5-hydroxy-hept-1(E)-en-3-yn-1-yl)9,10-se-co-preg-na-5(Z),7(E),10(19)-tri-ene (hereafter "Compound (E)"). A method of making Compound (E) is disclosed in EP 0708755. The chemical structure of Compound (E) is as follows:

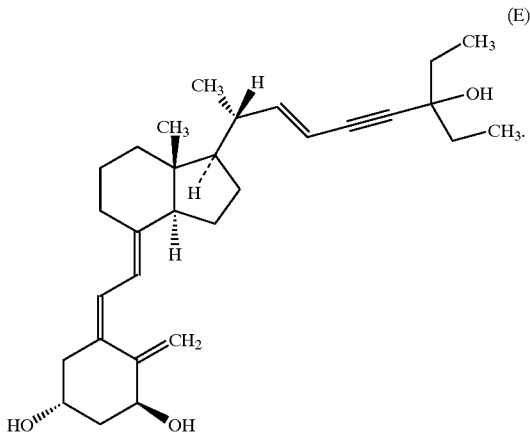

As discussed above with respect to the compound of Formula (I), Compound (A), Compound (B), Compound (C), Compound (D), and Compound (E) may optionally contain at least one asymmetric carbon atom. Accordingly, the compounds can exist as a mixture of enantiomers or as pure enantiomers. In addition, the compounds may optionally contain two or more asymmetric carbon atoms. These compounds can exist as racemic mixtures, diastereoisomeric mixtures or as individual enantiomers. The methods of the present invention cover all of these isomers in pure form and also as mixtures.

The compounds which may be utilized in accordance with the present invention can be readily prepared using standard organic synthetic methodology well known to one of ordinary skill in the art. The preparatory methods can vary, depending on the various definitions of the substituents and other chemical groups and moieties in the compounds, as will be apparent to one skilled in the art. For example, methods for making the compounds of Formula I, when Z is $Y_1$ are disclosed in detail by Bretting et al, U.S. Pat. No. 5,446,034 and PCT application WO 93/19044. Methods for making the compounds of Formula I, when Z is $Y_2$, $Y_3$, or $Y_4$, (Compounds (B), (C), and (D)), for example, are described in detail by Calverley et al, U.S. Pat. No. 5,374,629 and Calverley et al, U.S. Pat. No. 5,206,229. Methods for making the compounds of Formula I, when 7 is $Y_5$, are disclosed in detail by Gunmar Grue-Sorensen, U.S. Pat. No. 5,716,945 and EP 0708755.

The present invention also includes the use of prodrug forms of each of the compounds of Formula I, wherein one or more of the hydroxy groups in the compounds may be masked as groups which can be reconverted to hydroxy groups in vivo. Additionally, the above compounds wherein the group at the "X" position (or the corresponding "X" position in Compounds (B), (C) and (D)) is hydrogen may act as prodrugs because they are relatively inactive in vitro, but may be converted into active compounds by enzymatic hydroxylation after administration to the patient.

In view of the present disclosure, one skilled in the art may determine the dosage of the present therapeutic agents which will be most suitable for prophylaxis or treatment, and would know that the dosage may vary with the form of administration and the particular compound chosen, and also, that the dosage may vary with the particular patient and disease being treated. Generally, treatment is initiated with small dosages, which can then be increased by small increments until the optimum desired effect under the circumstances is achieved. For example, therapeutic dosages of the compounds described herein may generally range from about 0.001 μg (i.e., micrograms) to about 100 μg of vitamin D analogue or the like per kilogram of body weight, preferably from about 0.01 μg to about 10 μg per kilogram of body weight, more preferably from about 0.01 μg to about 1.0 μg per kilogram of body weight, even more preferably from about 0.01 μg to less than 1.0 μg per kilogram of body weight, taking into account the calcemic nature of the selected compound. The compounds may be administered in several different dosage units from once to several times a day. For example, about 0.1 μg to about 10 μg/kg of vitamin D analogue may be administered to a patient one or more times daily, preferably corresponding to a daily dose for an adult human being of about 0.05 μg to about 5 μg. Higher doses may be required for oral administration, again taking into account the calcemic nature of the selected compound.

While it is possible for the compounds described herein to be administered alone as the raw chemical, it is preferable to administer the compounds as a pharmaceutical composition. Generally, the active compound comprises from about 0.01% to 100% by weight of the pharmaceutical composition, while dosage units of the pharmaceutical composition contain from about 0.005 μg to about 100 μg of the active compound. The term "dosage unit" means a single dose which is capable of being administered to a patient, and which may be readily handled and packed, remaining as a physically and chemically stable unit dose comprising either the active compound as such or a mixture of the active compound with solid or liquid pharmaceutical diluents or carriers, as described herein.

The compounds described herein may also be administered in conjunction with exogenous neurotrophic factors, such as, by way of example and not limitation, IGF-1.

The methods of the present invention of treating neurodegenerative diseases, of inhibiting the degradation, dysfunction or loss, and/or enhancing the phenotype, of neural cells and/or neuronal processes, and of facilitating the endogenous production of neurotrophic factors, such as GDNF, NGF, NT—3, CTNF, NRT (including neurturin-like), and BDNF, can involve either in vitro or in vivo applications. In the case of in vitro applications, including cell culture applications, the compounds described herein can be added to the cells in cultures and then incubated. For example, cells which upregulate neurotrophic factors, such as GDNF, NGF, NT-3, CTNF, NRT, or BDNF, may be found by incubating the compounds of the present invention with a wide variety of cells, and then determining whether the neurotrophic factors or their respective mRNA's have been up-regulated.

With respect to in vivo applications, the compounds described herein can be administered to a patient in a variety of ways, including, for example, parenterally, orally, or intraperitoneally. Parenteral administration includes administration by the following routes: intravenous, intramuscular, interstitial, intra-arterial, subcutaneous, intraocular, intrasynovial, transepithelial, including transdermal, pulmonary via inhalation, ophthalmic, sublingual and buccal, topical, including ophthalmic, dermal, ocular, rectal, and nasal inhalation via insuflation or nebulization.

The active compounds may be orally administered, for example, with an inert diluent or with an assimilable edible carrier, they may be enclosed in hard or soft shell gelatin capsules, they may be compressed into tablets, or they may be incorporated directly with the food of the diet. For oral therapeutic administration, the active compounds may be incorporated with an excipient and used in the form of ingestible tablets, buccal tablets, troches, capsules, sachets, lozenges, elixirs, suspensions, syrups, wafers, and the like. The pharmaceutical composition comprising the active compounds may be in the form of a powder or granule, a solution or suspension in an aqueous liquid or non-aqueous liquid, or in an oil-in-water or water-in-oil emulsion.

The tablets, troches, pills, capsules and the like may also contain, for example, a binder, such as gum tragacanth, acacia, corn starch or gelating, excipients, such as dicalcium phosphate, a disintegrating agent, such as corn starch, potato starch, alginic acid and the like, a lubricant, such as magnesium stearate, and a sweetening agent, such as sucrose, lactose or saccharin, or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. The active compound may also be administered in the form of a bolus, electuary or paste.

The active compounds may be administered parenterally or intraperitoneally. Solutions of the compound as a free base or a pharmaceutically acceptable salt can be prepared in water mixed with a suitable surfactant, such as hydroxypropylcellulose. Dispersions can also be prepared in glycerol, liquid polyethylene glycols, and mixtures thereof, and in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It may be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size (in the case of a dispersion) and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and any of the other ingredients from those enumerated above. In the case of sterile powders for the preparation of sterile injectable solutions, the preferred methods of preparation are vacuum drying and the freeze drying technique.

Pharmaceutical compositions which are suitable for administration to the nose or buccal cavity include powder, self-propelling and spray formulations, such as aerosols, atomizers and nebulizers.

The therapeutic compounds of this invention may be administered to a mammal alone or in combination with pharmaceutically acceptable carriers or as pharmaceutically acceptable salts, as noted above, the proportion of which is determined by the solubility and chemical nature of the compound, chosen route of administration and standard pharmaceutical practice. The compositions may also contain other therapeutically active compounds which are usually applied in the treatment of the diseases and disorders discussed herein. Treatments using the present compounds and other therapeutically active compounds may be simultaneous or in intervals.

Serum calcium levels may also be taken into consideration with the administration of the compounds of the present invention, for example, by taking into account dietary considerations. For example, a high-calcium diet can increase serum calcium levels, and a low-calcium diet can decrease serum calcium levels. Therefore, one skilled in the art can manipulate the dose range of the low calcemic compounds of the present invention, for example, by adjusting the calcium intake in the patient's diet. Such manipulation is within the purview of one skilled in the art.

The present invention is also directed to methods of treating peripheral neuropathy using the compounds of the present invention. Peripheral neuropathy generally refers to a disorder that affects the peripheral nerves, most often manifested as one or a combination of motor, sensory, sensorimotor or autonomic neural dysfunction. The wide variety of morphologies exhibited by peripheral neuropathies can each be uniquely attributed to an equally wide variety of causes. For instance, peripheral neuropathies can be genetically acquired, can result from a systemic disease, or can be induced by a toxic agent, such as therapeutic drugs, antineoplastic agents, contaminants in foods or medicines, and environmental and industrial pollutants. Without intending to be bound by any theory of the invention, it is believed that the present compounds facilitate the production of the neurotrophic factor NT-3. NT-3 is useful in the treatment of peripheral neuropathy due to the presence of NT-3 receptors on neurons in the PNS. The neuropathy can be attributed to an external agent, e.g., acrylamide, or a disease and/or hereditary disorder. Agents, diseases and hereditary disorders which lead to peripheral neuropathy are described in U.S. Pat. No. 5,420,112, the disclosure of which is hereby incorporated by reference herein in its entirety.

In another embodiment of the present invention, the low calcemic vitamin D analogues may be used to treat multiple sclerosis. U.S. Pat. No. 5,716,946 to DeLuca, the disclosure of which is hereby incorporated herein by reference in its entirety, discloses methods for using vitamin D which may be applied to the present invention to treat multiple sclerosis. The method of the present invention advantageously uses vitamin D analogues that surprisingly have low calcemic activity.

Thus, the present invention is directed, inter alia, to methods of treating neurodegenerative diseases and/or disorders by utilizing low calcemic vitamin D analogues which facilitate the endogenous production of neurotrophic factors, which neurotrophic factors inhibit the degradation, dysfunction or loss of neural cells and/or neuronal processes and/or enhance the phenotype of neural cells, which cellular degradation, dysfunction or loss results from or is attributed to such disease or disorder. The present invention is also directed to methods of treating peripheral neuropathy by utilizing low calcemic vitamin D analogues, which facilitate the production of neurotrophic factors, which neurotrophic factors inhibit the degradation or loss of neural cells, which cellular degradation or loss results from or is attributed to such neuropathy. The present invention may be carried out by administering low calcemic vitamin D analogues, or compounds that facilitate the production of neurotrophic factors, such as GDNF, NRT (including neurturin-like), NT-3, NGF, CTNF, BDNF, or combinations thereof to a patient.

The present invention is also directed to the use of low calcemic vitamin D analogues, including, for example, the compounds of Formula (I) such as Compound (A), Compound (B), Compound (C), Compound (D), or Compound (E) in the manufacture of a medicament for the prevention and/or treatment of neurodegenerative diseases, including, for example, Alzheimer's disease, amyotrophic lateral sclerosis ("ALS" or "Lou Gehrig's disease"), Parkinson's disease, Huntington's disease, ischaemia, stroke, and aging, generally, and peripheral neuropathy. The low calcemic vitamin D analogues useful in the present invention may also be used in the manufacture of a medicament for the treatment of multiple sclerosis.

EXAMPLES

The following examples are presented for purposes of elucidation and not limitation. The examples are not intended, nor are they to be construed, as limiting the scope of the disclosure or claims.

Example 1: Preparation of Pharmaceutical Compositions

Compound (A) was obtained from Leo Pharmaceutical Products, Ltd., Ballerup, Denmark. The method described in U.S. Pat. No. 5,446,034, the disclosure of which is hereby incorporated by reference herein in its entirety, can be followed to prepare 1(S),3(R)-dihydroxy-20(R)-(1-ethoxy-5-ethyl-5-hydroxy-2-heptyn-1-yl)-9,10-seco-pregna-5(Z),7(E),10(19)-triene ("Compound (A)"): NMR: $\delta$=0.55 (s,3H), 0.90 (t, 6H), 1.02 (d, 3H), 1.20 (t, 3H), 1.15–2.10 (m, 21H), 2.31 (dd, 1H), 2.39 (m, 2H), (dd, 1H), 2.83 (dd, 1H), 3.31 (m, 1H), 3.75 (m, 1H), 4.17 (m, 1H), 4.22 (m, 1H, 4.43 (m, 1H), 5.00 (m, 1H), 5.33 (m, 1H), 6.02 (d, 1H), 6.37 (d, 1H).

For making a tablet, Compound (A) (0. 1 $\mu$g), lactose (75 mg) and starch (12 mg) were mixed to a homogeneous state in a suitable mixer and moistened with a 5% aqueous solution of methylcellulose (2 mg) 15 cps. The mixing was continued until granules were formed. The wet granulation was passed through a suitable screen and dried to a water content of less than 1% in a suitable dryer, e.g., fluid bed or drying oven. The dried granulation was passed through a 1 mm screen and mixed to a homogeneous state with sodium carboxymethyl cellulose (10 mg). Magnesium stearate (1 mg) was added, and the mixing was continued for a short period of time. Tablets with a weight of 200 mg were produced from the granulation by means of a suitable tableting machine.

For making a capsule, Compound (A) was dissolved in arachis oil to a final concentration of 1 $\mu$g/ml oil. Ten parts by weight of gelatin, 5 parts by weight of glycerin, 0.08 parts by weight potassium sorbate, and 14 parts by weight distilled water were mixed together with heating and formed into soft gelatin capsules. The capsules were then filled with 100 $\mu$l of the oil solution of Compound (A).

A pharmaceutical composition for injection may be prepared by dissolving 1% of Compound (A) in water (water for injection to make 100%). The solution may be made isotonic with sodium chloride (q.s.). The solution can thereafter be filled into ampoules and sterilized.

Example 2: Vitamin D Receptor Binding and Calcemic Activity

Compounds which evidence binding affinity of $\leq 10^{-7}$ M to a vitamin D receptor are considered to be vitamin D analogues. For testing binding to the vitamin D receptor, isolated receptors for $1\alpha,25(OH)_2D_3$ from the intestinal epithelium of rachitic chickens were purchased from Amersham (U.K.). 500 $\mu$l of receptor protein was incubated with $^3$H-1 $\alpha,25(OH_2)D_3$ and increasing concentrations of test compound were added. Bound and free $^3$H-$1\alpha,25(OH_2)D_3$ were then separated on dextran-coated charcoal, samples were centrifuged and the supernatants containing the receptor-bound $^3$H-$1\alpha,25(OH_2)D_3$ were counted in a liquid scintillation counter. The concentration of the test compound resulting in 50% displacement of bound $^3$H-$1\alpha,25(OH_2)D_3$ was calculated, and the potency of the compounds relative to $1\alpha,25(OH_2)D_3$ in the actual experiment was determined.

TABLE 1

| Compound | Receptor Binding $K_d$ (M) | Calcemic Activity (%) |
| --- | --- | --- |
| $1\alpha,25(OH)_2 D_3$ | $10^{-12} - 10^{-11}$ | 100 |
| (A) | $2 \times 10^{-10}$ | 24 |
| (B) | $2 \times 10^{-10}$ | 1 |
| (C) | $2 \times 10^{-12}$ | 8 |
| (D) | $5 \times 10^{-12}$ | 20 |
| (E) | $3 \times 10^{-10}$ | 20 |

For determining calcemic activity, LEW/MOL female rats (130–170 g) were administered test compounds daily for 7 days by oral gavage. Control rats received the vehicle. Each group consisted of 3 rats. Blood was collected by cardiac puncture on day 7. Serum calcium was determined using a Hitachi 705 autoanalyzer and calcium in urine was assessed as $\mu$mol/day, as shown in Tables 2A–2D. The potency relative to $1\alpha,25(OH)_2D_3$ was calculated using the actual values obtained in each separate experiment, and are shown in Table 1 above. The "Calcemic Activity (%)" of the compounds was determined in rats in vivo as previously described by, for example, Binderup et al, *Biochem Parmacol.*, 37:889–895 (1988).

TABLE 2A

| | Compound (A) | |
| --- | --- | --- |
| Compound | Dosage $\mu$g/kg/day p.o. | Calcium in Serum mmol/l ± S.D. |
| None (vehicle) | — | 2.46 ± 0.06 |
| $1\alpha,25(OH)_2 D_3$ | 0.5 | 2.71 ± 0.08 |
| (A) | 0.1 | 2.52 ± 0.02 |
| | 1.0 | 2.62 ± 0.02 |
| | 10 | toxic |

TABLE 2B

Compound (B)

| Compound | Dosage µg/kg/day p.o. | Calcium in Serum mmol/l ± S.D. |
|---|---|---|
| None (vehicle) | — | 2.57 ± 0.06 |
| 1α,25(OH)$_2$ D$_3$ (B) | 0.5 | 2.66 ± 0.10 |
|  | 10 | 2.51 ± 0.05 |
|  | 50 | 2.59 ± 0.02 |
|  | 100 | 2.59 ± 0.04 |

TABLE 2C

Compound (C)

| Compound | Dosage µg/kg/day p.o. | Calcium in Serum mmol/l ± S.D. |
|---|---|---|
| None (vehicle) | — | 2.68 ± 0.03 |
| 1α,25(OH)$_2$ D$_3$ (C) | 0.5 | 2.77 ± 0.03 |
|  | 0.1 | 2.71 ± 0.07 |
|  | 1.0 | 2.66 ± 0.06 |
|  | 10 | 2.82 ± 0.05 |

TABLE 2D

Compound (D)

| Compound | Dosage µg/kg/day p.o. | Calcium in Serum mmol/l ± S.D. |
|---|---|---|
| None (vehicle) | — | 2.51 ± 0.09 |
| 1α,25(OH)$_2$ D$_3$ (D) | 0.5 | 2.71 ± 0.03 |
|  | 0.1 | 2.59 ± 0.08 |
|  | 5.0 | 2.90 ± 0.06 |
|  | 10 | 3.19 ± 0.16 |

TABLE 2E

Compound (E)

| Compound | Dosage µg/kg/day p.o. | Calcium in Serum mmol/l ± S.D. |
|---|---|---|
| None (vehicle) | — | 2.51 ± 0.09 |
| 1α,25(OH)$_2$ D$_3$ (E) | 0.5 | 2.71 ± 0.03 |
|  | 0.1 | 2.41 ± 0.01 |
|  | 1.0 | 2.42 ± 0.04 |
|  | 10 | 2.38 ± 0.03 |

For the fimbria fornix lesion studies, serum calcium was determined by the following method. Sprague Dawley rats (200–300 g) were dosed as described below. Blood was collected from the animals after sacrifice and allowed to clot at room temperature for 3–10 minutes; cells were pelleted in a clinical centrifuge. Serum was then analyzed for calcium levels, using a commercially available kit in accordance with manufacturer recommendations (Sigma, calcium binding reagent, cat. no. 587-A, with Accutrol™ normal standards, cat. no. A2034).

Example 3: Induction of mRNA Expression in Rats

Young adult male Sprague Dawley rats (250–350 g) were administered Compound (A), Compound (E), or a vehicle (80% propylene glycol (human formulation grade; Spectrum Quality Products, Inc., Gardena, Calif., catalog #PR130-55003) and 20% phosphate buffer, pH 9.2) at doses ranging from 0.1 to 5.5 µg/kg daily by oral gavage for eight days. Five hours after the last dose, the animals were sacrificed by decapitation. Each brain was quickly removed and chilled in ice-cold saline. The brain was cut into 2 mm thick coronal sections. Portions of the hippocampus, encompassing the CA1 region, and the medial septum were removed by punching 2 mm$^3$ sections using a calibrated tissue punch. Punched sections were immediately frozen on dry ice and then stored at −70° C. RNA was prepared from dissected tissue pieces.

Punches of tissue were homogenized in 750 ml RNA-zolB™ (Bioteex Laboratories, Houston, Tex.) using a homogenizer (Tekmar, Germany) until fully homogenized and then 250 µl RNAzilB™ was added. Typically, punches from the corresponding regions of brains of 2 to 3 animals were combined together. RNA was prepared as recommended by the manufacturer (Biotecx Laboratories). Following isopropanol precipitation, RNA was reprecipitated with ethanol and finally resuspended in 25–50 µL of water. Concentration of RNA was measured spectrophotometrically and the quality of RNA was visualized on a nondenaturing agarose gel. Equal amounts of RNA, usually 1–2 µg, were reverse transcribed using Superscript II™ (Gibco BRL), as recommended by the manufacturer. The assay was terminated by incubation at 95° C. 1 min. at 55–60° C. (depending on the primer set) and 2 min. at 72° C. Typically 20–28 cycles were employed (each assay was in a linear range). After the assay, samples were electrophoresed on 5% nondenaturing acrylamide gels. Gels were dried and the resulting labeled bands were visualized on a phosphorimager (Storm 840, Molecular Dynamics, Sunnyvale, Calif.). The following primers were used:

Nerve Growth Factor (NGF). Primers were designed against the rat sequence.
(5') 5'-CTAAACTTCAGCATTCCC-3' (SEQ ID NO:1)
(3') 5'-AAAGGTGTGAGTCGTGGT-3' (SEQ ID NO:2)

Neurturin-like (NRT-like). Primers were designed against the murine sequence.
(5') 5'-GTGGAGCTTCGAGAACTTTCTCCC-3' (SEQ ID NO:3)
(3') 5'-TAGCGGATGTGTACGTCCAGGAAGGACACC-3' (SEQ ID NO:4)

Glial Cell-Line Derived Neurotrophic Factor (GDNF). Primers were designed against the rat sequence.
(5') 5'-GAAGTTATGGGATGTCGTGGCTG-3' (SEQ ID NO:5)
(3') 5'-TCTGGCCTCTGCGACCTTTCCC-3' (SEQ ID NO:6)

Neurotrophin 3 (NT-3). Primers were designed against the rat sequence.
(5') 5'-GCTGAGTGACAGCACCCCTT-3' (SEQ ID NO:7)
(3') 5'-GCGCCAGCCTACGAGTTTGT-3' (SEQ ID NO:8)

Brain-Derived Neurotrophie Factor (BDNF). Primers were designed against the rat sequence.
(5') 5'-GCAAACATGTCTATGAGGGT-3' (SEQ ID NO:9)
(3') 5'-GGTCAGTGTACATACACAGG-3' (SEQ ID NO:10)

Ciliary Neurotrophic Factor (CNTF). Primers were designed against the rat sequence.
(5') 5'-dTGGCTAGCAAGGAAGATTCGT-3' (SEQ ID NO: 11)
(3') (5')dACGAAGGTCATGGATGGACCT-3' (SEQ ID NO:12)

FIG. 1 shows the expression of NGF mRNA, GDNF mRNA, NRT-like mRNA in the septum. FIG. 1 also shows the expression of NGR mRNA, GDNF mRNA, NT-3 mRNA, and BDNF mRNA in the hippocampus. The GAPDH in FIG. 1 served as an internal control. The results in FIG. 1 indicate that at doses of 0.3, 1.0 and 3.0 μg/kg, Compound (A) facilitated the production of NRT-like mRNA, GDNF mRNA, NT-3 mRNA, and BDNF mRNA. Unexpectedly, at the low calcemic dose of 0.3 μg/kg, Compound (A) did not facilitate the production of NGF mRNA.

Compound (A) facilitated the production of NGF mRNA at doses of 1.0 and 3.0 μg/kg. However, a 3.0 μg/kg dose of Compound (A) was hypercalcemic to the animals. The 1.0 μg/kg dose of Compound (A) did not increase serum calcium after 2 weeks of dosing. However, 28-day toxicology studies demonstrated that 1 μg/kg of Compound (A) was hypercalcemic to female, but not male, Sprague Dawley rats (data not shown). Therefore, based upon these results 1.0 μg/kg of Compound (A) is a hypercalcemic dose when considered in toto.

Figure 2A:
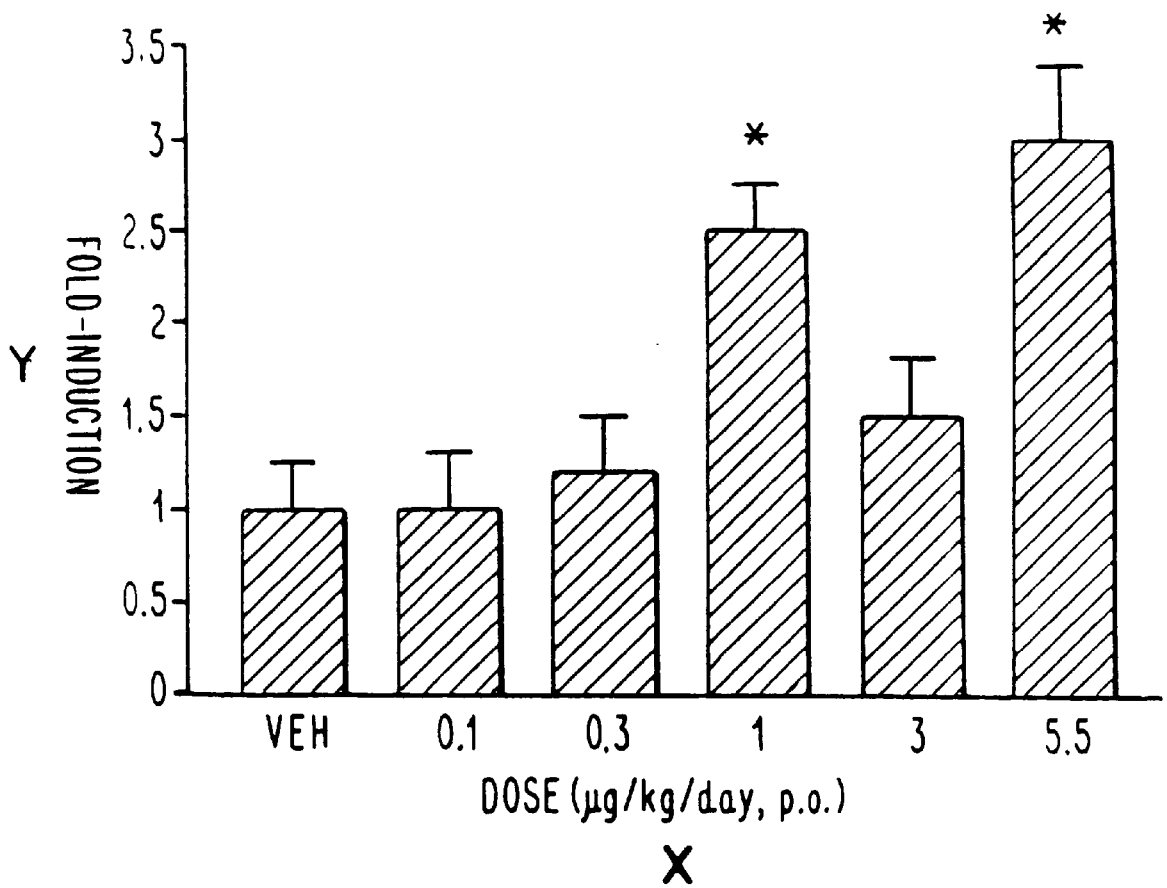
FIG. 2A is a graphical representation showing the expression of NGF mRNA in a rat septum versus dosage rate of Compound (E).
Figure 2B:
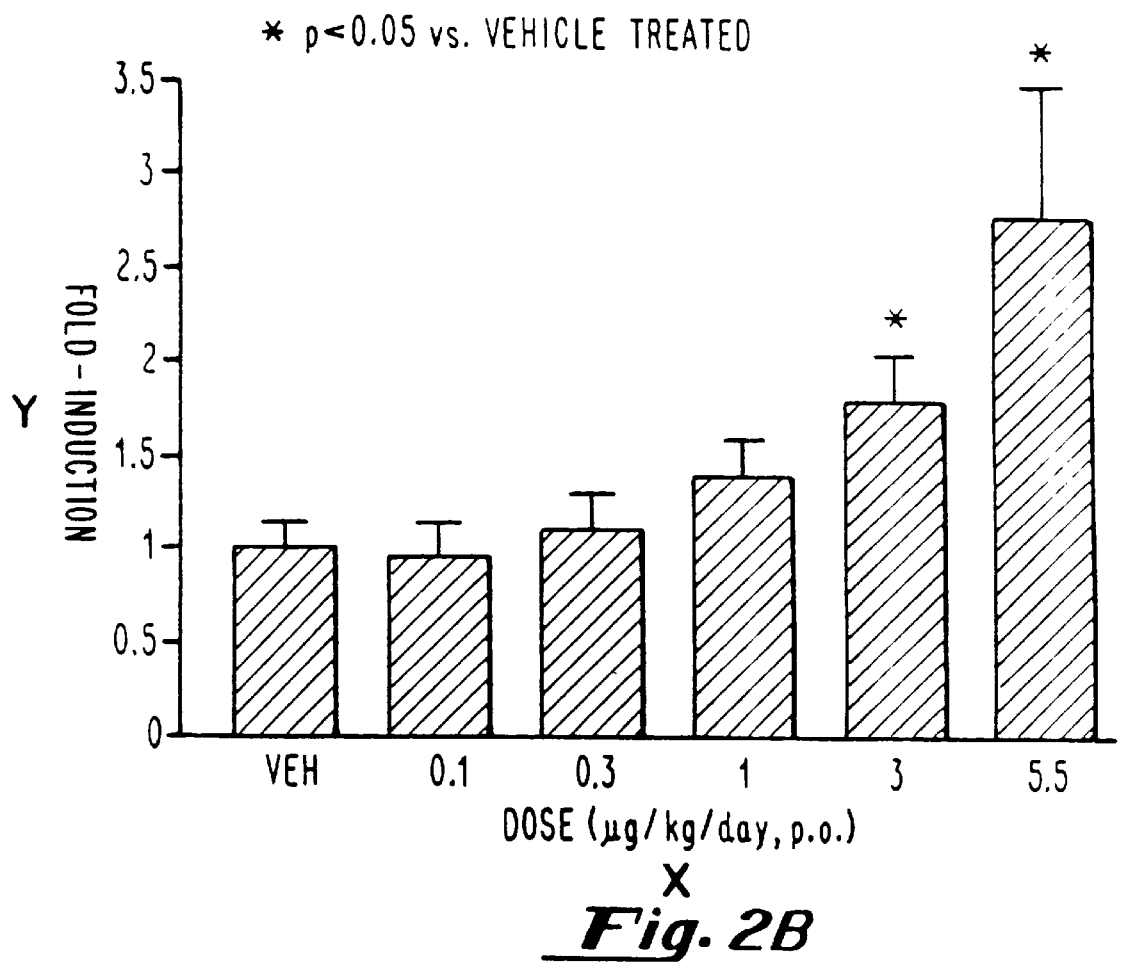
FIG. 2B is a graphical representation showing the expression of CNTF mRNA in a rat septum versus dosage rate of Compound (E).

FIG. 2A shows the fold-induction (Y-axis) of NGF mRNA in the rat septum versus dosage (X-axis) of Compound E. FIG. 2B shows the fold-induction (Y-axis) of CNTF mRNA in the rat septum versus dosage (X-axis) of Compound E. The results in FIGS. 2A and 2B indicate that at doses of 0.3, 1.0, 3.0, and 5.5 μg/kg, Compound (E) facilitated the production of NGF mRNA and CTNF mRNA (respectively). The production of NGF mRNA and CTNF mRNA generally increased with increasing dosage of Compound (E).

Example 4: Fimbria Fornix Studies

Figure 3:
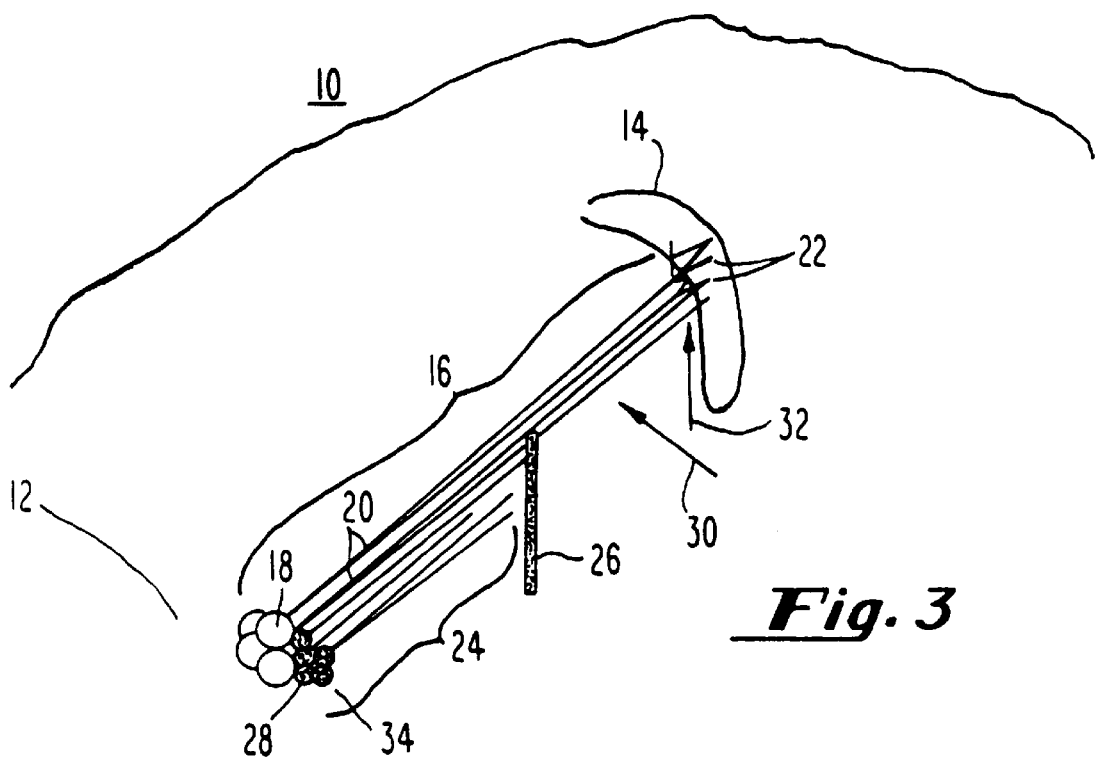
FIG. 3 is a schematic representation of the fimbria fornix lesion model discussed in Example 4.

The fimbria fornix lesion model is an established protocol for assessing cholinergic neuronal survival in the basal forebrain. A schematic representation of the fimbria fornix lesion model is set forth in FIG. 3. FIG. 3 shows a region of the brain 10 that includes the basal forebrain 12 and the hippocampus 14. Contained within the region of the brain 10 are cholinergic neurons 16. A healthy cholinergic neuron has a cell body 18, and one or more axons 20. Each of the axons 20 have a free end, referred to as a terminal 22, that extends into the hippocampus 14. In the fimbria fornix lesion model, damaged cholinergic neurons 24 are produced by transecting a portion of the axons 20 at a location 26 between the hippocampus 14 and the cell body 18. As a result of this transection, damaged cell bodies 28 are produced that no longer have cholinergic axons 30 and terminals 32. These damaged cell bodies 28, also lose cholinergic cell body markers 34 and stop producing ChAT. The fimbria fornix lesion model is used to study methods of restoring ChAT production, such as through stimulating increased production of ChAT in the healthy cholinergic neurons, and/or through restoring normal functioning of the damaged cholinergic neurons 24.

For the studies described herein, animals were anesthetized with pentobarbital and placed in a stereotaxic apparatus. The skull was opened on the left side, a knife was positioned 1.2 mm posterior to bregma and 0.6 mm lateral to the midline. The knife was lowered to 4.5 mm below the dura into the brain and moved laterally 2 mm partially transecting the fimbria fornix. After 14 days of administration of the test compounds by oral gavage, the hippocampus was removed and homogenized. The resulting hippocampal extracts were tested for ChAT activity as an indicator of basal forebrain cholinergic neuronal survival and/or function, using procedures as described, for example, by Srebo, B. et al, $Life\ Sci.$ 12:261 (1972).

Based upon previous data indicating that efficacious doses for $1\alpha,25(OH)_2D_3$ are calcemic, Compounds (A), (B), (C), (D), and (E) determined to be exemplary of low calcemic vitamin $D_3$ analogues, were utilized for the following experiments.

A. Oral Administration of Compounds (A), (B), (C), (D), and (E)

Figure 4:
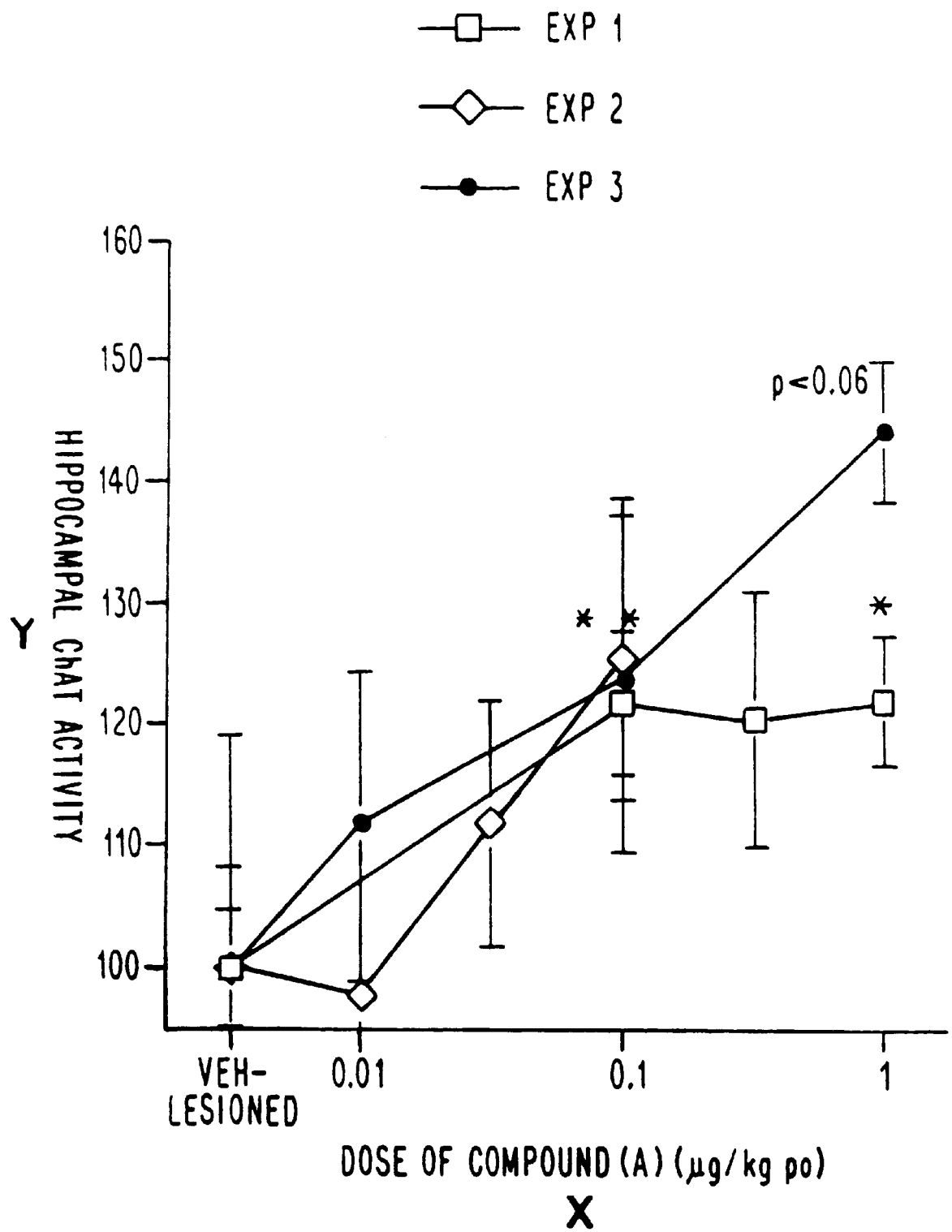
FIG. 4 is a graphical representation of hippocampal ChAT activity of fimbria fornix lesioned animals treated with Compound (A), as compared to a control.
Figure 5:
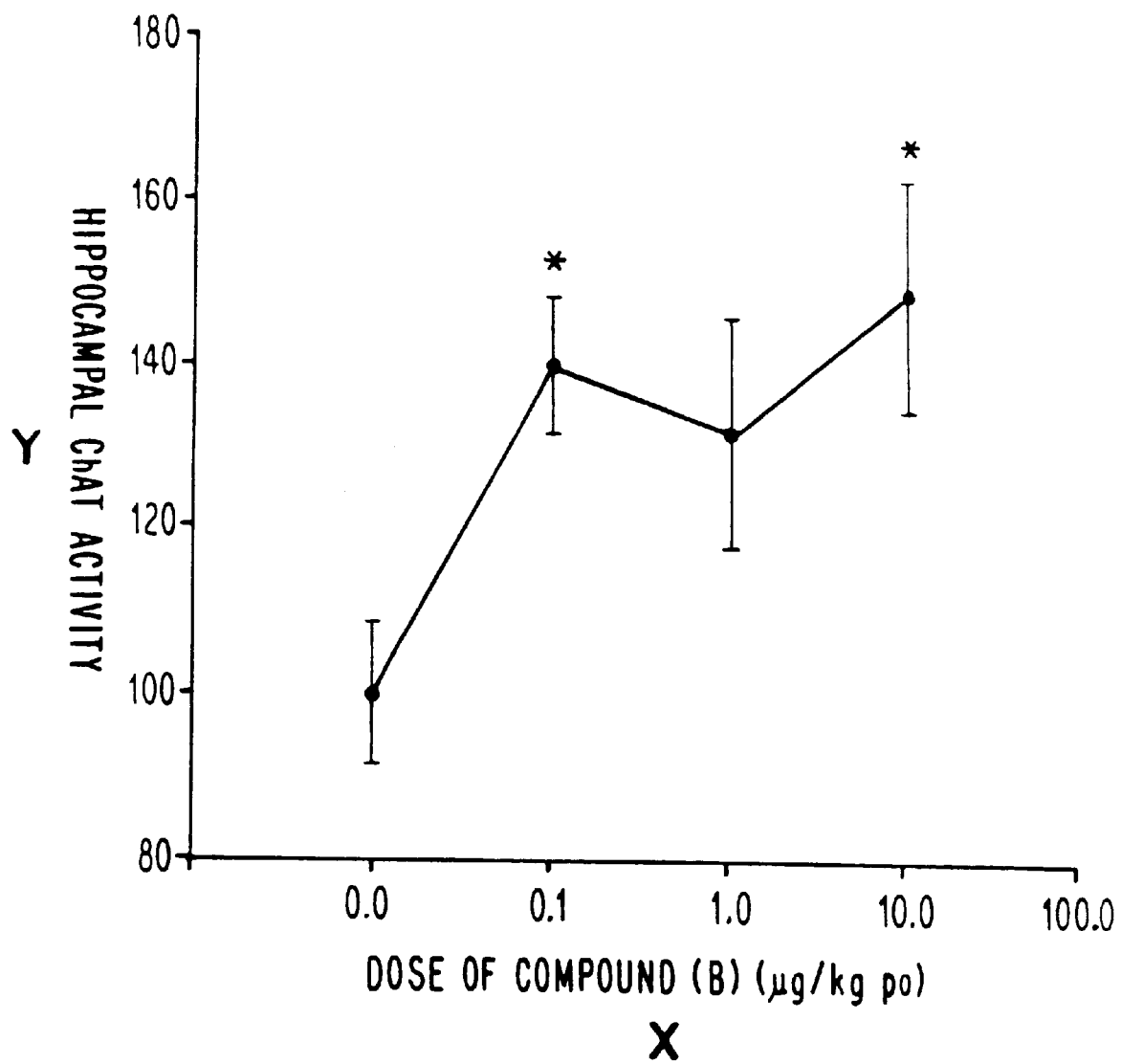
FIG. 5 is a graphical representation of ChAT activity of fimbria fornix lesioned animals treated with Compound (B), as compared to a control.
Figure 6:
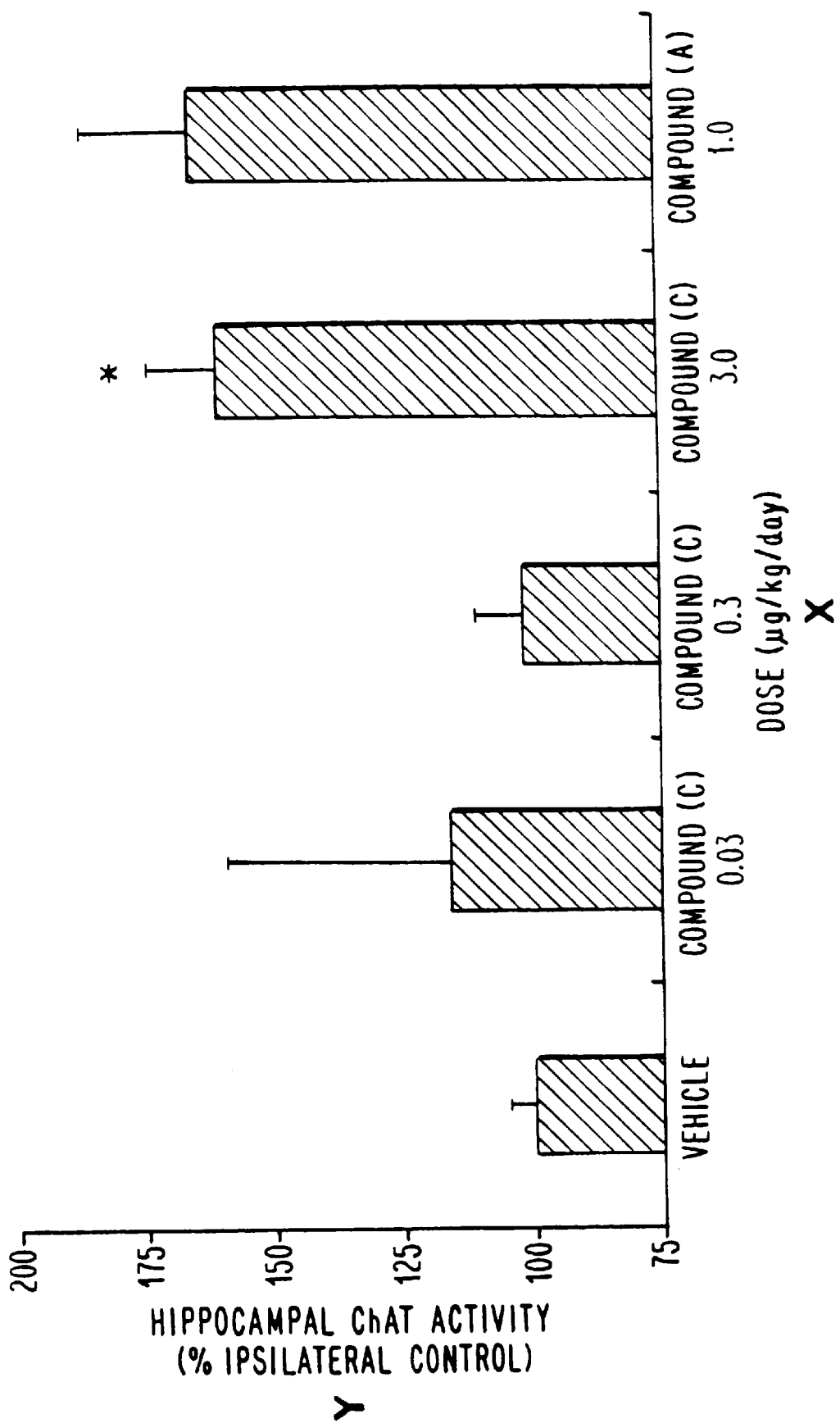
FIG. 6 is a graphical representation of hippocampal ChAT activity of fimbria fornix lesioned animals treated with Compound (C), as compared to a control.
Figure 7:
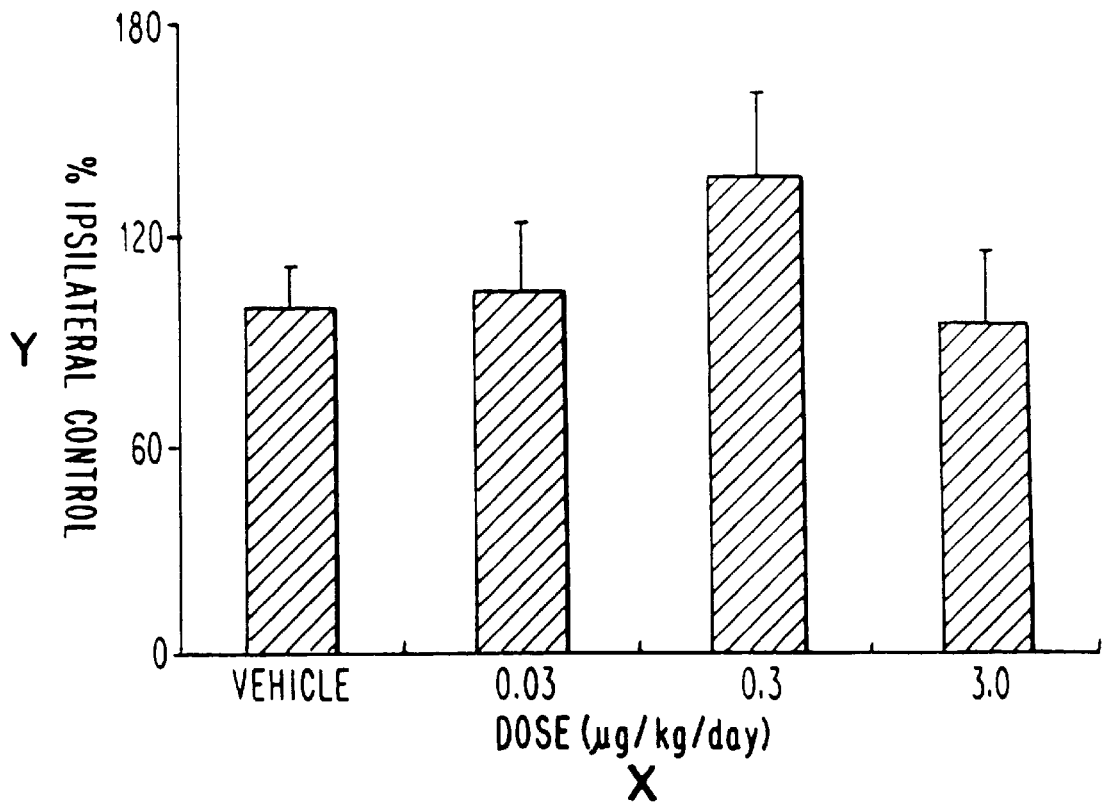
FIG. 7 is a graphical representation of hippocampal ChAT activity of fimbria fornix lesioned animals treated with Compound (D), as compared to a control.
Figure 8:
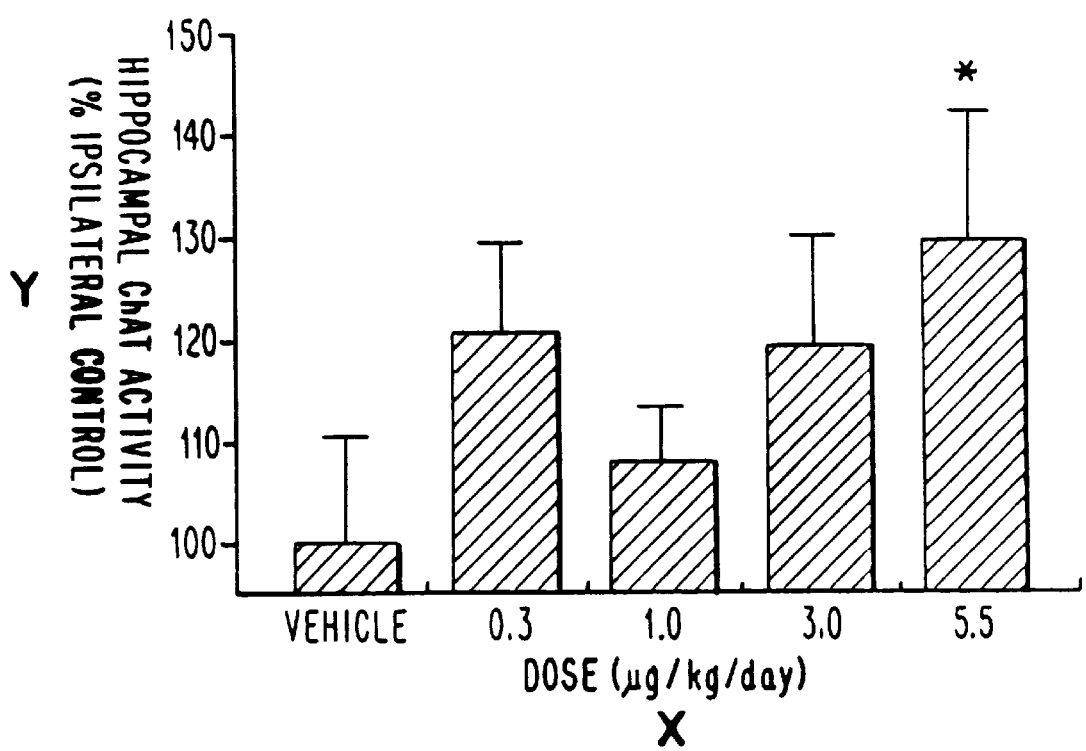
FIG. 8 is a graphical representation of hippocampal ChAT activity of fimbria fornix lesioned animals treated with Compound (E), as compared to a control.

Compounds (A), (B), (C), (D) and (E) were dosed daily by oral gavage over a period of 14 days beginning at the day of, or 3 days prior to, lesion at various dose levels. The doses tested were those shown in previous studies not to increase serum calcium levels (i.e., see Tables 2A–2D, supra.) ChAT activity of the hippocampi from fimbria fornix lesioned animals was assessed; additionally, serum was collected from the animals and calcium levels were assessed. FIGS. 4 to 8 show the hippocampal ChAT Activity (Y-axis) as a function of dose (X-axis) for Compounds (A), (B), (C), (D), and (E) respectively (* indicates statistically significant, $p<0.05$, compared to vehicle-treated fimbria fornix lesioned controls, using paired Student-3 s t test, assuming equal variance). The hippocampal ChAT activity is expressed as a percentage of the hippocampal ChAT activity of the ipsilateral control side (i.e., lesion control) in FIGS. 4 to 8. In FIG. 4, lesion sizes resulting in a 23% (Experiment 1), 40% (Experiment 2), and 48% (Experiment 3) reduction of ChAT activity as compared to the unlesioned side of the brain were studied in addition to dosage rate. The results presented in FIGS. 4 to 8 indicate that there was significant increase in CHAT activity in the lesioned animals treated with Compounds (A), (B), (C), (D) (E) as compared to lesioned animals receiving propylene glycol (n>20). Additionally, based upon serum calcium levels (data not shown), the results indicate that the ChAT activity results were obtained at low calcemic dose levels.

B. Cholinergic Cell Number

Fimbria fornix lesioned animals treated orally with Compound (A) (n=10) or vehicle (n=10) were assessed using acetyl cholinesterase staining of both the lesion area and hippocampal formation. Animals received either Compound (A) (1 μg/day) or vehicle via oral gavage (14 days). Four animals from the vehicle group and 5 animals from the Compound (A) group having comparable lesions were selected for evaluation of the effect of numbers of cholinergic cell bodies by immunohistochemical reaction with polyclonal antibody to ChAT, using a procedure as described, for example, by Batcherlor et al., $J\ Comp.\ Neurol.$ 284:187 (1989).

Figure 9:
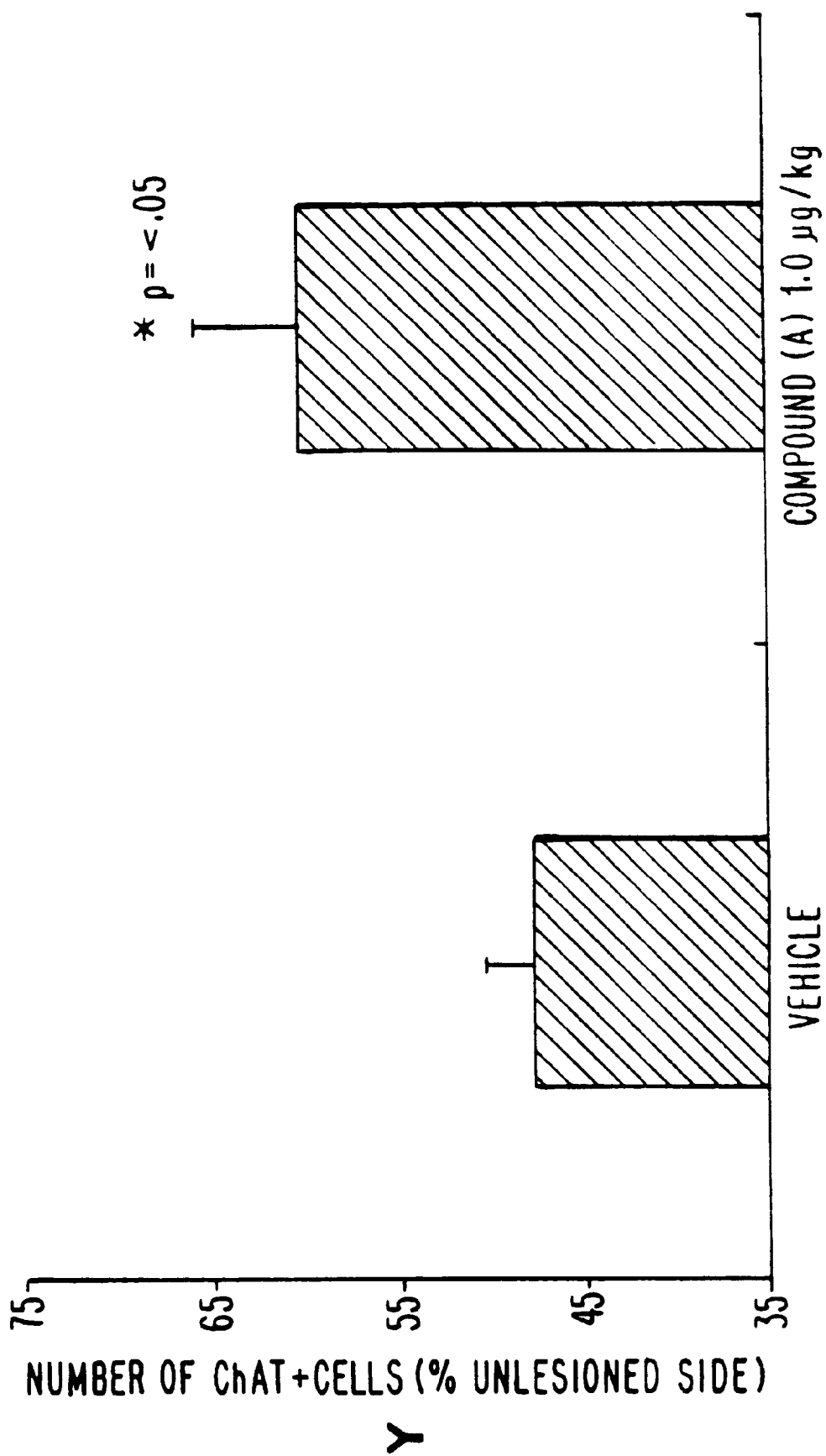
FIG. 9 is a graph evidencing the increase in septal neurons expressing ChAT in partially fimbria fornix lesioned animals treated with Compound (A) as compared to velicle-treated controls.

Coronal sections were cut at 30 mm with a cryostat and collected throughout the medial septum. Every fourth section was processed for the visualization of ChAT positive neurons. Approximately 12 sections were assessed per brain. Cholinergic cells were counted and expressed as a ratio of lesioned to unlesioned control side. FIG. 9 shows the number of ChAT producing cells (Y-axis) as a percentage of the ChAT producing cells of the unlesioned side for the vehicle group and the Compound (A) group. The results, presented in FIG. 9, indicate that lesioned animals treated with Compound (A) have an approximate 30% increase in the number of cholinergic cells as compared to vehicle treated lesioned animals.

Example 5: Behavioral Studies

Figure 10:
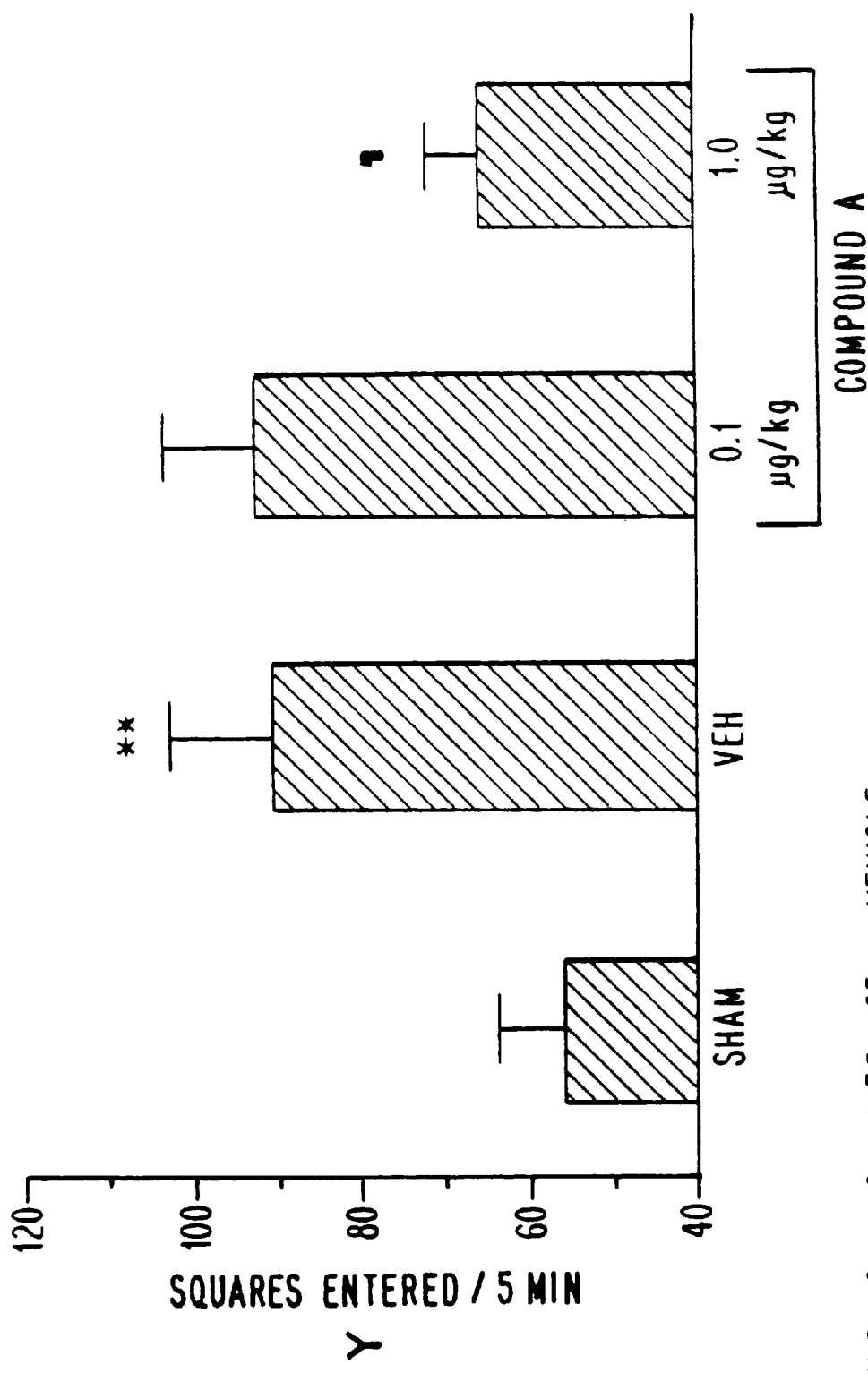
FIG. 10 is a graph evidencing that Compound (A) reduces locomotor activity caused by fimbria fornix lesions in rats.

To determine whether low calcemic doses of vitamin $D_3$ analogs would improve lesion-induced behavioral deficits, Compound (A) (0.1 and 1.0 μg/kg/day) was administered orally once a day (26 days) to rats having bilateral lesions of the fimbria-fornix. Bilateral lesions of the fimbria-fornix cause rats to become hyperactive. To test for hyperactivity, rats were placed in a box marked with squares, where it was observed how many squares the rats entered in a five minute period. FIG. 10 shows the squares entered per 5 minutes (Y-axis) versus a Sham group of unlesioned rats, a vehicle group of untreated lesioned rats, Compound (A) group rats fed 0.1 µg/kg/day, and Compound (A) group rats fed 1.0 µg/kg/day. As can be seen from FIG. 10, unlesioned rats (Sham) entered less than 60 squares in a five minute period, while a fimbria-fornix lesioned rat (Veh) entered more than 80 squares in a five minute period. Rats treated with 1.0 µg/kg/day of Compound (A) exhibited reduced locomotor activity when compared to rats that did not receive any treatment. The results indicate that a low calcemic dose of a vitamin $D_3$ analog prevents hyperactivity in animals subjected to fimbria fornix lesioning.

Example 6: Peripheral Neuropathy

Figure 11A:
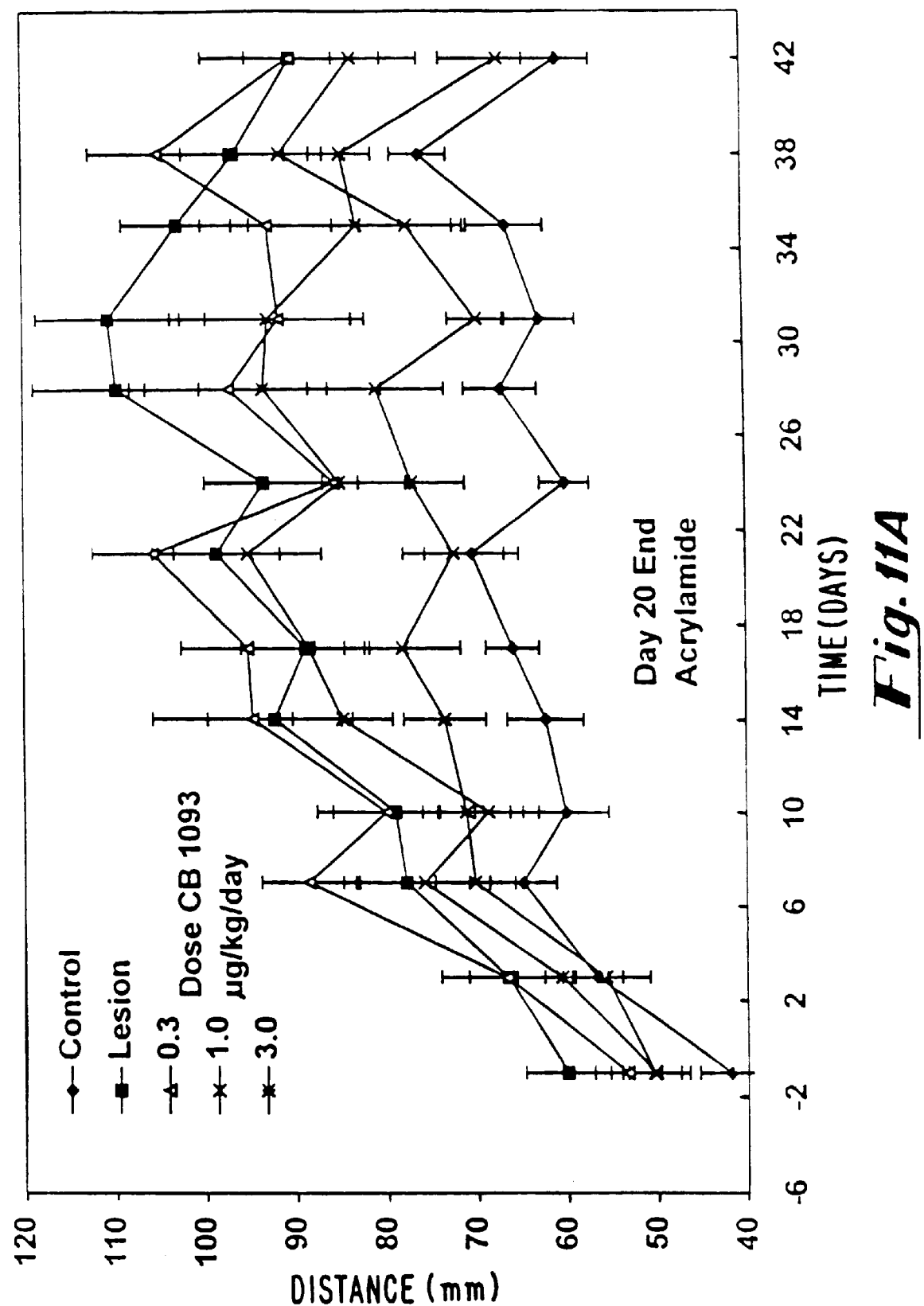
FIGS. 11A, 11B and 11C are graphs showing that orally administered Compound (A) decreases landing foot spread in rats with acrylamide-induced peripheral neuropathy. In particular.
Figure 11B:
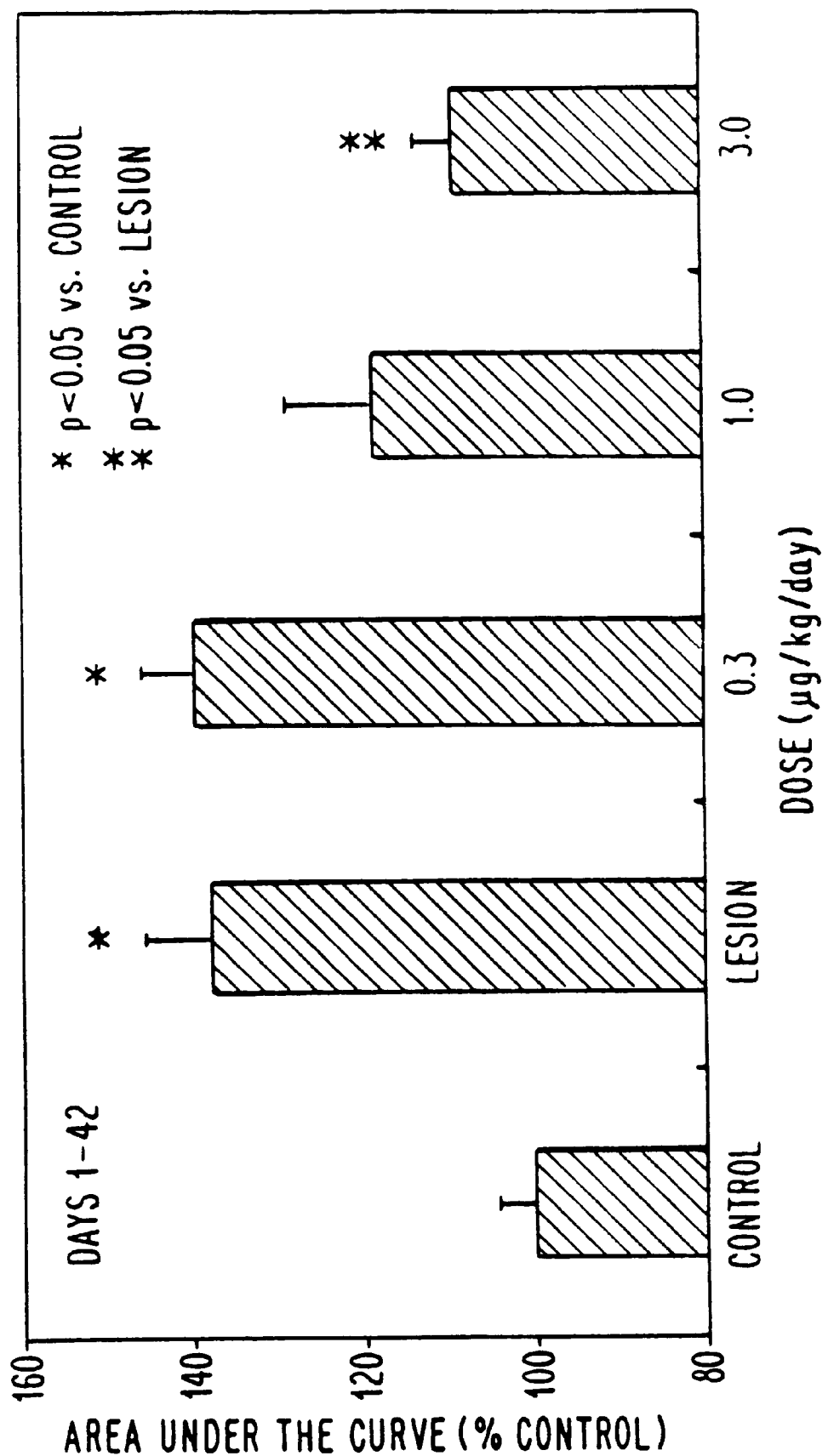
Figure 11C:
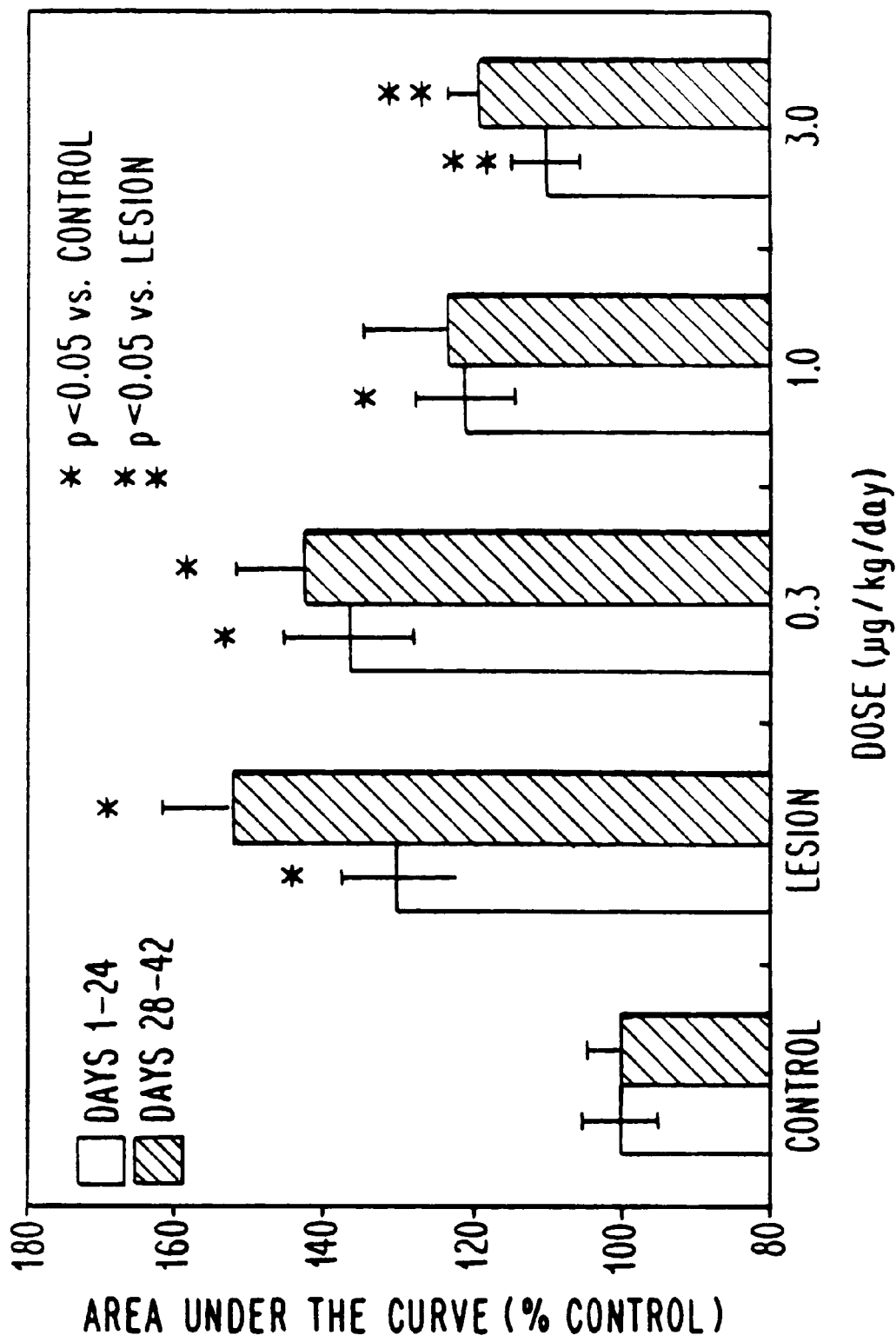

Peripheral neuropathy was induced in rats by the administration of the neurotoxin acrylamide, 50 mg/kg, IP, 3×/week. The acrylamide treatment occurred during the first three weeks of the experiment. After acrylamide was discontinued, the animals were allowed to recover for an additional 3–5 weeks. The ability of Compound (A) or Compound (B) to either slow the onset of peripheral neuropathy, reduce the severity of the peripheral neuropathy or enhance the recovery from peripheral neuropathy was determined. The compounds were administered either orally (Compound (A)) or via subcutaneous Alzet mini-pumps (I month model)(Compounds (A) and (B)) beginning 3 days prior to the first dose of acrylamide. Compound (A) was administered orally at doses of 0.3, 1.0 and 3.0 µg/kg/day and by mini-pump at doses of 10, 55, 100, 330 and 550 ng/day. Compound (B) was administered by mini-pump at doses of 10, 33, 100, 330 and 1000 ng/day. These dose ranges were selected to limit toxicity and to bracket the dose range used in fimbria fornix lesion experiments. The mini-pumps were replaced at the end of the fourth week so that the test compound was on board for the duration of the experiment. The complete time course of orally administered Compound (A) is shown in FIG. 11A. In FIG. 11B, the data from FIG. 11A was averaged. Treatment with Compound (A) at dose of 3.0 µg/kg/day resulted in statistically significant decrease in landing foot spread. This change occurred during the onset of the lesion (days 1–24) and were sustained through the recovery phase (days 24–42; see FIG. 11C).

Figure 12A:
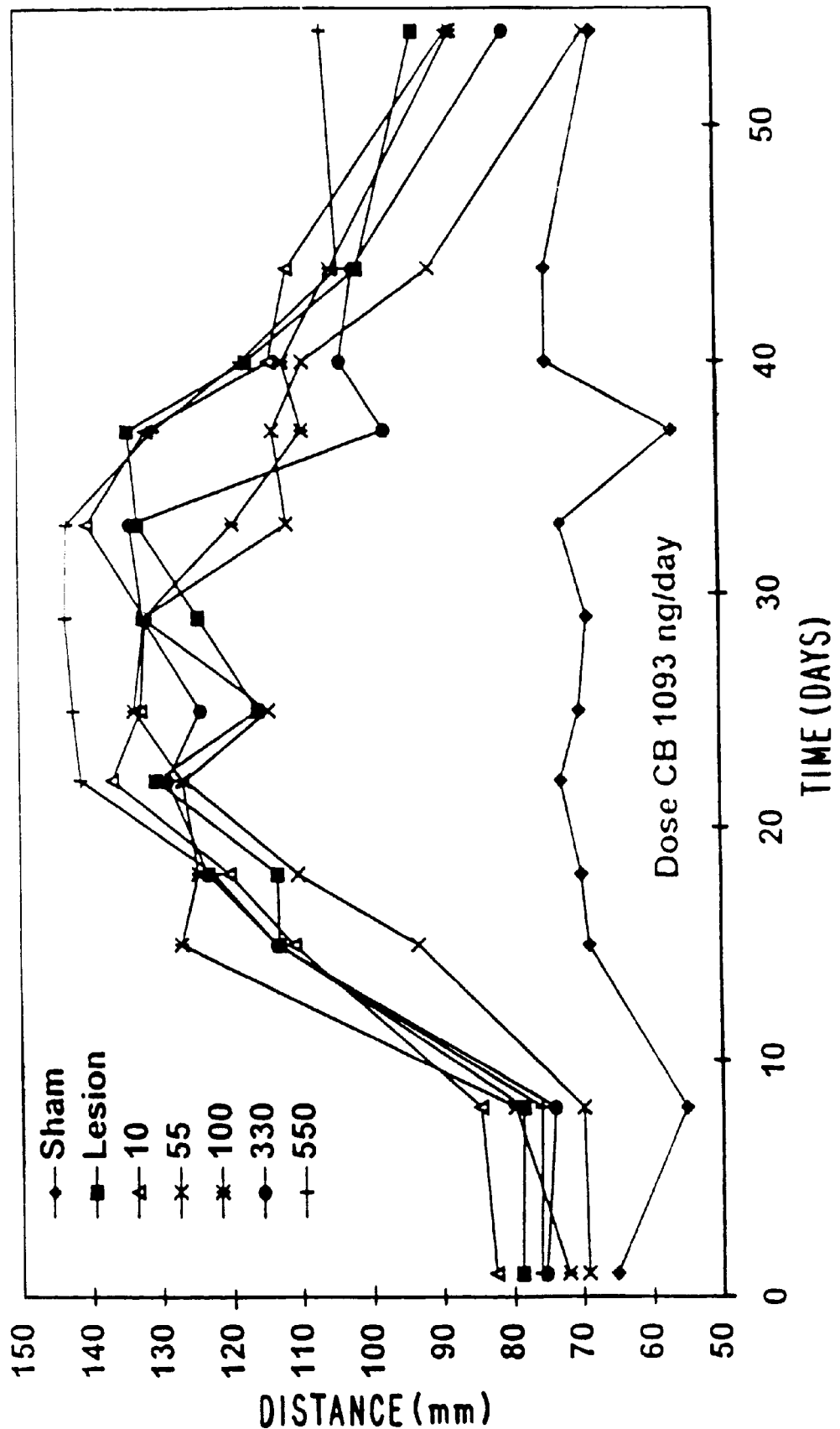
FIGS. 12A and 12B are graphs showing that Compound (A) administered by mini-pumps decreased landing foot spread during the recovery period of acrylamide-induced peripheral neuropathy. In particular.
Figure 12B:
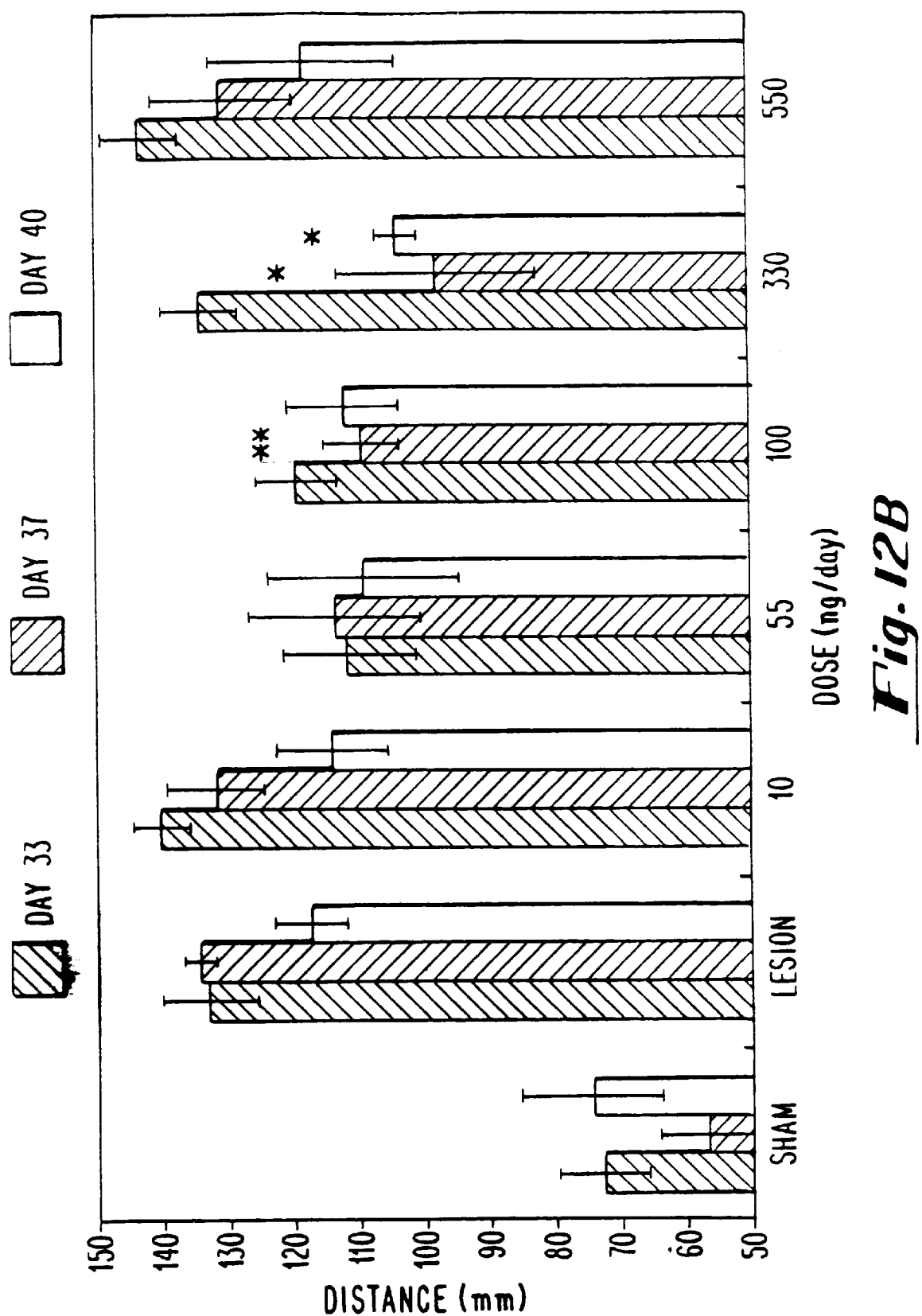

When administered continuously via mini-pumps, Compound (A) was effective in reducing landing foot spread, but only during the recovery period. FIG. 12A shows the complete dose response and time course, and FIG. 12B shows the results on days 33, 37 and 40 (all during the recovery period).

Thus, based upon the data, oral administration appears to be the optimal route of dosing Compound (A) in this model (vs mini-pump). Oral administration of Compound (A) produced dose-dependent effects on both the severity of the acrylamide-induced peripheral neuropathy as well as the ability of the animals to functionally recover from the lesion, while mini-pump administration improved recovery. This data is consistent with Compound (A) acting as a sprouting agent in this model.

Figure 13A:
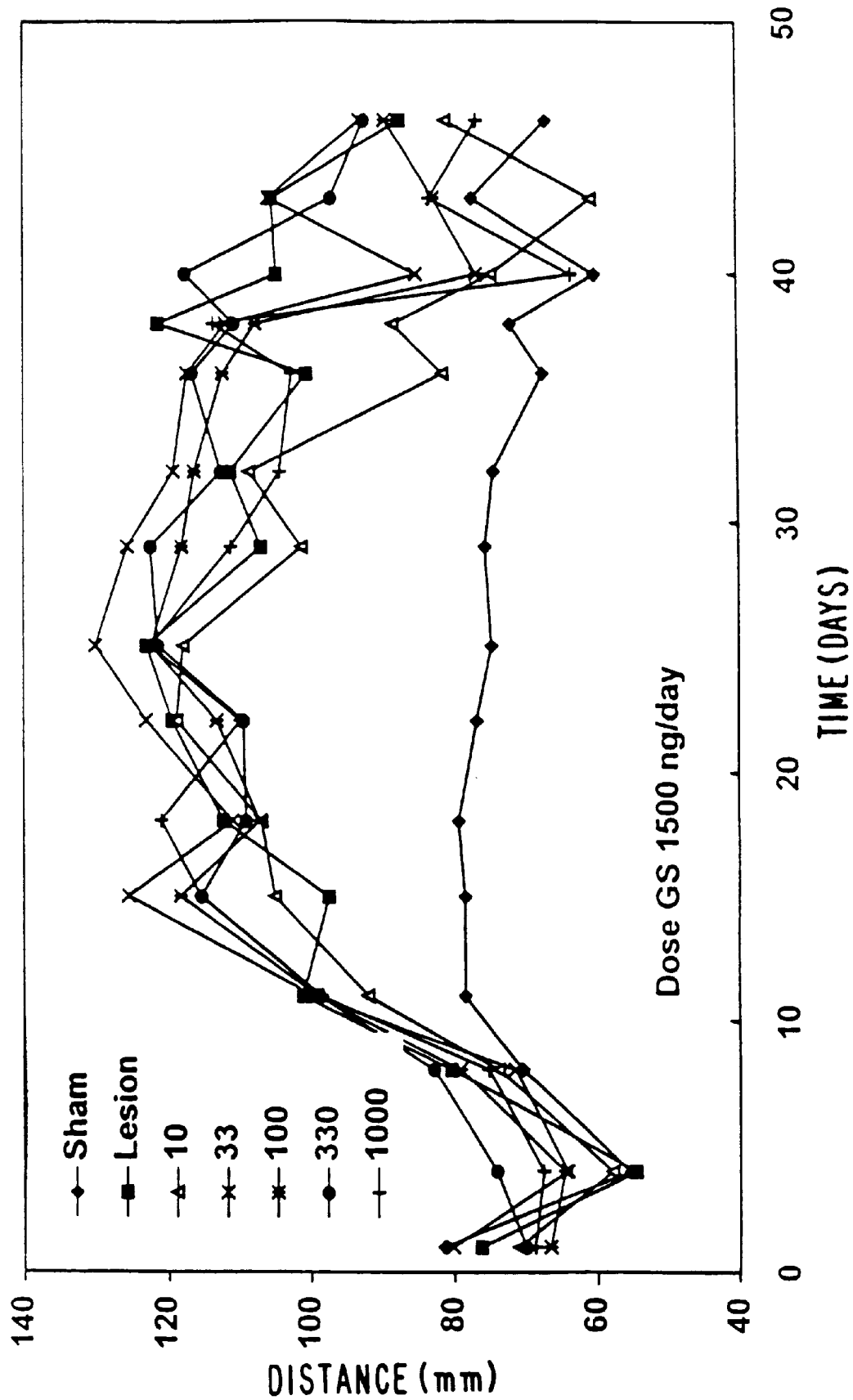
FIGS. 13A and 13B are graphs showing that Compound (B) administered by mini-pumps decreased landing foot spread during the recovery period of acrylamide-induced peripheral neuropathy. In particular.
Figure 13B:
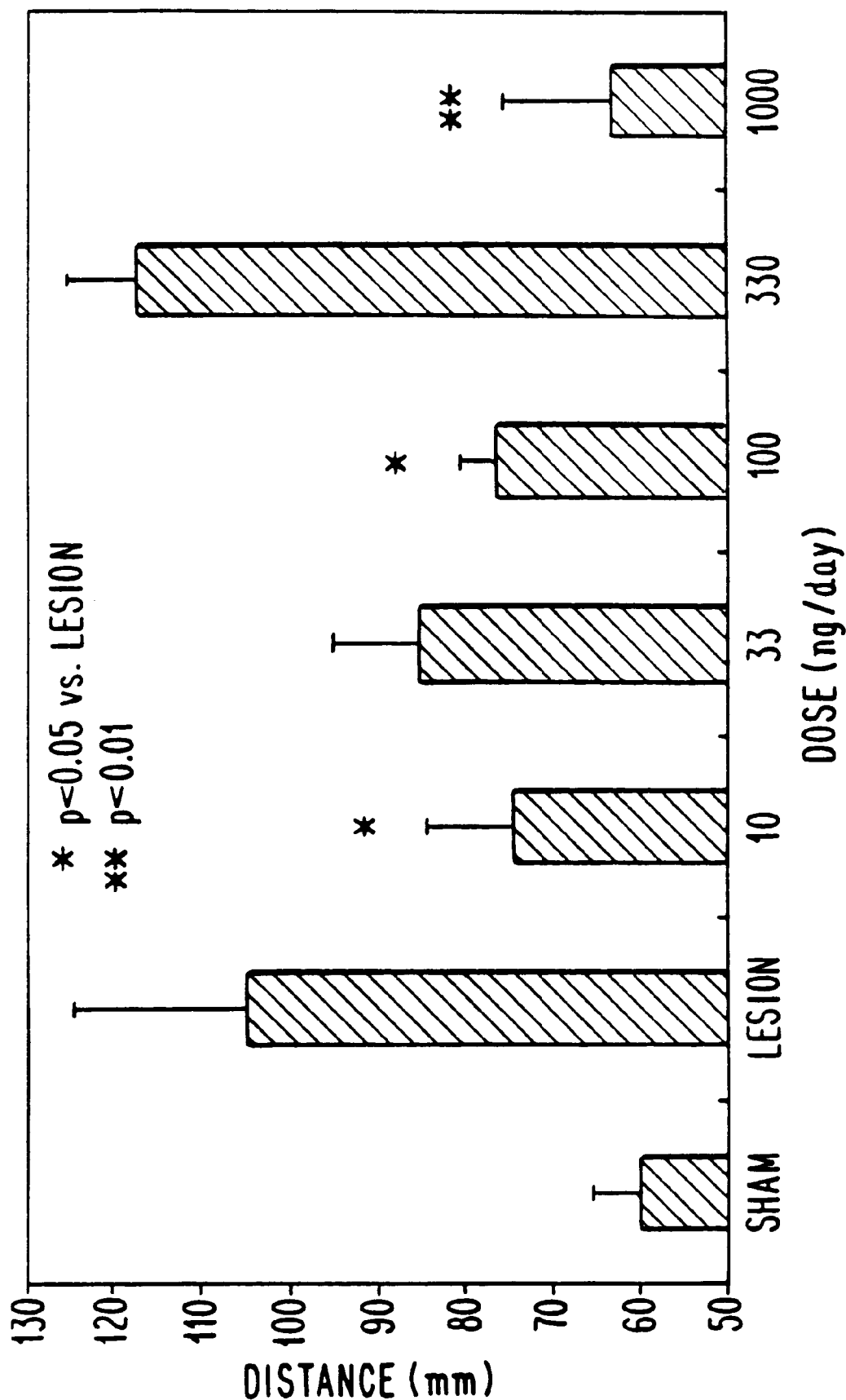

As can be seen in FIGS. 13A and 13B, Compound (B) increased the recovery from acrylamide-induced peripheral neuropathy. The landing foot spread time course and the profile for the recovery phase of the acrylamide-induced peripheral neuropathy is shown in FIG. 13A. Treatment with Compound (B) at doses of 10, 100 or 1000 ng/day resulted in a statistically significant decrease in landing foot spread on day 40, as shown in FIG. 13B. In fact, the landing foot spread of animals treated with the lowest dose of Compound (B) (10 ng/day) had returned to sham levels by day 36.

Orally administered Compound (A) prevented the development of acrylamide-induced peripheral neuropathy, while continuously pumped Compounds (A) and (B) did not prevent the development of the acrylamide-induced peripheral neuropathy, an effect upon the recovery from the lesion was apparent from both compounds. This suggests that these compounds may act by speeding the repair process by an unknown mechanism, such as sprouting or direct effects upon muscle or nerves.

Example 7: Induction of mRNA Expression in Primates

Twelve monkeys, ranging in weight from 2.0 Kg to 4.7 Kg, were divided into three groups of 4 animals each: the vehicle group (i.e., control), group dosed with 10 µg/kg/day, and group dosed with 30 µg/kg/clay. The monkeys were dosed orally for 8 days with Compound (A) and were sacrificed 5 hours after the last dosing. Brain regions were dissected and quick frozen. The dissected septi were divided into 3 preparations and two of the three regions of septum were analyzed. Total RNA was prepared and reverse transcribed and gene expression was assessed using polymerase chain reaction by the following procedure.

Total RNA was prepared by homogenizing sections of tissue in 750 µl RNAzolB™ (Biotecx Laboratories, Houston, Tex.) using a homogenizer (Tekmar, Germany) until fully homogenized and then 250 µl RNAzilB™ was added. RNA was prepared as recommended by the manufacturer (Biotecx Laboratories). Following isopropanol precipitation, RNA was reprecipitated with ethanol and finally resuspended in 25–50 mL of water. Concentration of RNA was measured spectrophotometrically and the quality of RNA was visualized on a nondenaturing agarose gel. Equal amounts of RNA, usually 1–2 µg, were reverse transcribed using Superscript II (Gibco BRL), as recommended by the manufacturer. Each PCR assay was repeated at least twice. The assay was terminated by incubation at 95° C., 1 min. at 55–60° C. (depending on the primer set) and 2 min. at 72° C. Typically 20–32 cycles were employed (each assay was in a linear range). After the assay, samples were electrophoresed on 5% nondenaturing acrylamide gels. Gels were dried and the resulting labeled bands were visualized on a phosphorimager (Storm 840, Molecular Dynamics, Sunnyvale, Calif.).

An average of 4 PCR assays (two assays for each gene for two cDNA sets) were used in determining the induction of mRNA expression. To assure that PCR assays were within the linear range of the reaction, the linear range for each gene and each cDNA preparation was determined using serial dilutions of cDNAs. The following primers were used:

Nerve Growth Factor (NGF). Primers were designed against the rat sequence.

(5') 5'-CTAAACTTCAGCATTCCC-3' (SEQ ID NO:1)

(3') 5'-AAAGGTGTGAGTCGTGGT-3' (SEQ ID NO:2)

Glial Cell-Line Derived Neurotrophic Factor (GDNF). Primers were designed against the rat sequence.

(5') 5'-GAAGTTATGGGATGTCGTGGCTG-3' (SEQ ID NO:5)

(3') 5'-TCTGGCCTCTGCGACCTTTCCC-3' (SEQ ID NO:6)

Figure 14A:
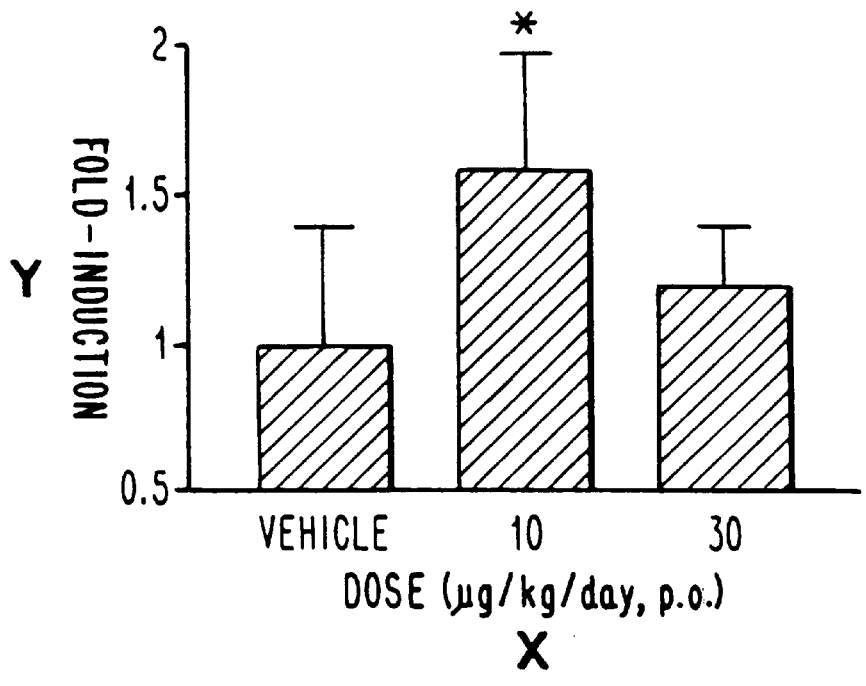
FIG. 14A is a graphical representation showing the expression of NGF mRNA in a primate septum versus dosage rate of Compound (A).
Figure 14B:
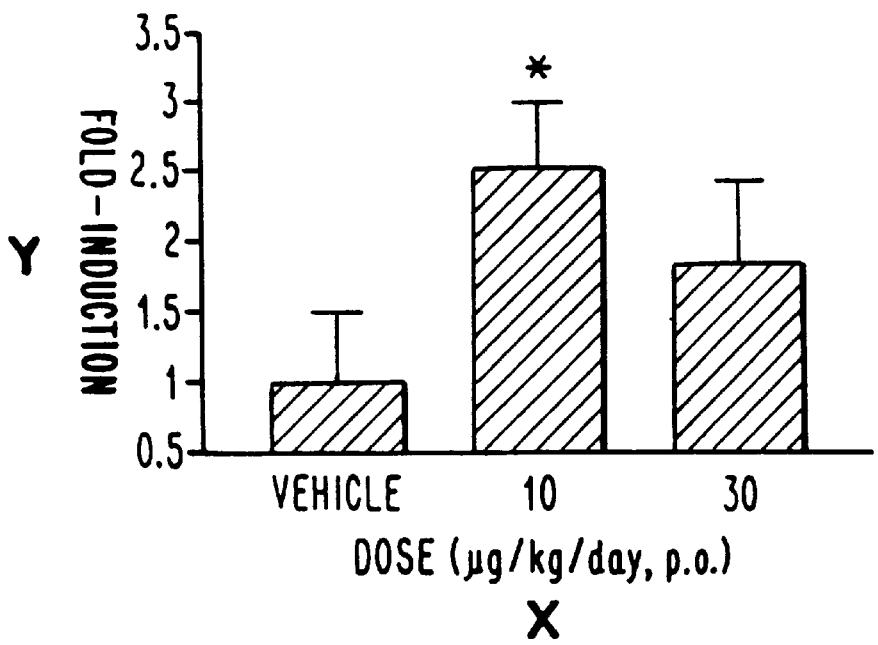
FIG. 14B is a graphical representation showing the expression of GDNF mRNA in a primate septum versus dosage rate of Compound (A).

FIG. 14A shows the fold induction (Y-axis) of NGF mRNA of the primate septum versus dosage (X-axis) of Compound (A). FIG. 14B shows the fold induction (Y-axis) of GDNF mRNA of the primate septum versus dosage (X-axis) of Compound (A). The results in FIGS. 14A and 14B indicate that at doses of 10 μg/kg/day and 30 μg/kg/day, Compound (A) facilitated the production of NGF mRNA and GDNF mRNA (respectively). The production of NGF mRNA and GDNF mRNA was greatest at a dosage of 10 μg/kg/day for Compound A. The doses fed to the primates did not increase serum calcium levels and were not hypercalcemic doses.

The disclosure of each patent, patent application and publication cited or described in this document is hereby incorporated by reference herein in its entirety.

Although the invention has been set forth in considerable detail, those skilled in the art will appreciate that numerous changes and modifications can be made to the preferred embodiments of the invention and that such changes and modifications may be made without departing from the sprit and scope of the invention.

What is claimed is:

1. A method of treating neurodegenerative diseases or disorders comprising administering to a patient a compound of Formula (I):

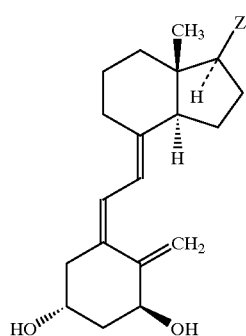

wherein Z is selected from the group consisting of

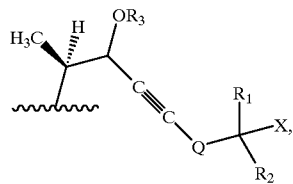

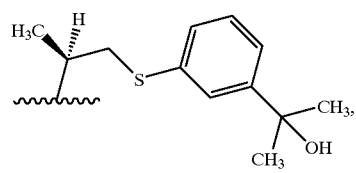

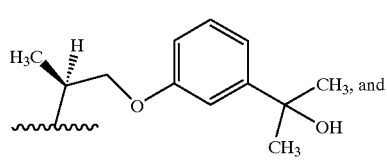

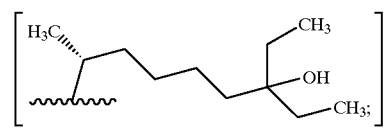

and

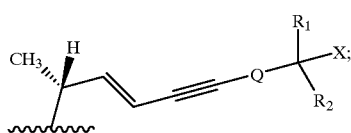

and wherein

X is a hydrogen atom or a hydroxy group;

$R_1$ and $R_2$ each independently represents a hydrogen atom or a C1–C6 alkyl group, or $R_1$ and $R_2$, taken together with the carbon atom bearing the X group, to form a C3–C8 cyclic ring;

$R_3$ is a hydrogen atom or a C1–C10 alkyl group; and

Q is a single bond or a C1–C8 alkylene group.

2. The method of claim 1, wherein the neurodegenerative disease or disorder is selected from the group consisting of Alzheimer's disease, amyotrophic lateral sclerosis, Huntington's disease, Parkinson's disease, ischaemia and stroke.

3. The method of claim 2, wherein the neurodegenerative disease or disorder is Alzheimer's disease.

4. The method of claim 1, wherein Z in the compound of Formula (I) is $Y_1$:

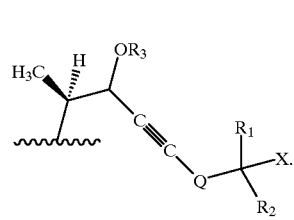

5. The method of claim 4, wherein the compound of Formula (I) is Compound (A):

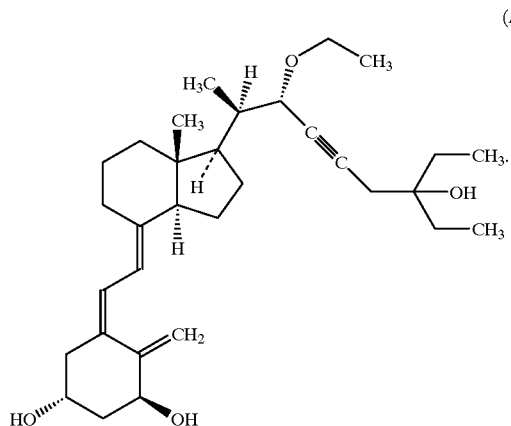

6. The method of claim 1, wherein the compound of Formula I is Compound (B):

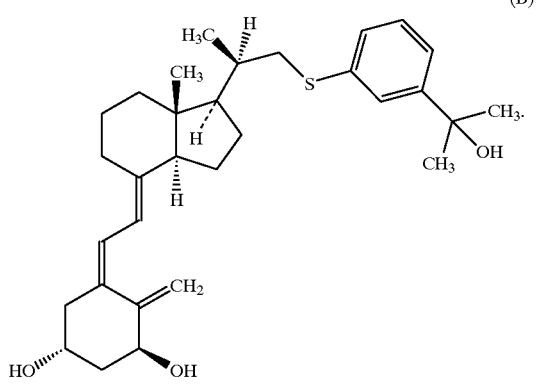

7. The method of claim 1, wherein the compound of Formula I is Compound (C):

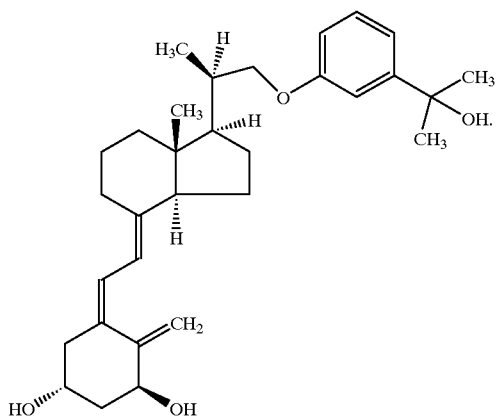

8. The method of claim 1, wherein Z in the compound of Formula (I) is $Y_5$:

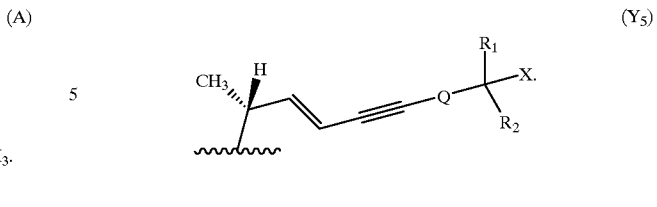

9. The method of claim 8, wherein the compound of Formula (I) is Compound (E):

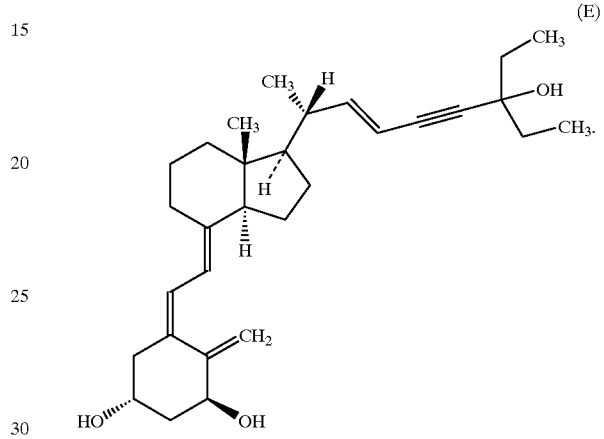

10. The method of claim 1, wherein the compound is administered in an amount of about 0.01 µg to about 10 µg per kilogram body weight.

11. The method of claim 1, wherein $R_1$ or $R_2$ represents a $C_1$–$C_6$ alkyl group substituted with one or more deuterium atoms or fluorine atoms.

12. The method of claim 1, wherein $R_1$ and $R_2$ together with the carbon atom bearing the X group form a $C_3$–$C_8$ ring substituted with one or more deuterium atoms or fluorine atoms.

13. The method of claim 1, wherein $R_3$ is a $C_1$–$C_{10}$ alkyl group substituted with one or more deuterium atoms or fluorine atoms, or $YR_4$, wherein Y is —CO—, —COO—, —COS—, —CS—, —CSO—, —CSS—, —SO— or —SO— and $R_4$ is a hydrogen atom or a $C_1$–$C_{10}$ alkyl group that is optionally substituted with one or more deuterium atoms or fluorine atoms.

14. The method of claim 1, wherein Q is a $C_1$–$C_8$ alkylene group substituted with one or more deuterium atoms or fluorine atoms.

15. A method of facilitating production of a neurotrophic factor selected from the group consisting of GNDF, NT-3, NRT, CTNF, NGF, BDNF, and combinations thereof, comprising administering to a patient a compound of Formula (I):

(I)

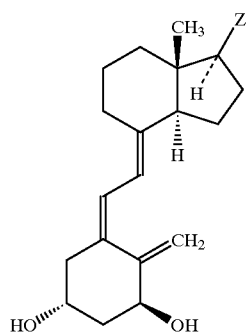

wherein Z is selected from the group consisting of

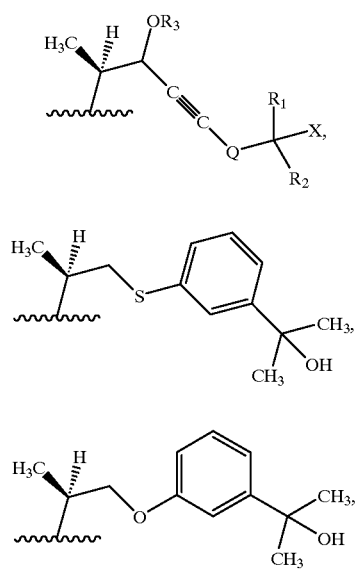

and

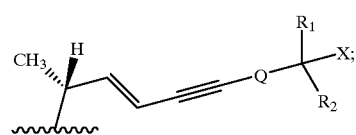

and wherein
X is a hydrogen atom or a hydroxy group;
$R_1$ and $R_2$ each independently represents a hydrogen atom or a C1–C6 alkyl group, or $R_1$ and $R_2$, taken together with the carbon atom bearing the X group, to form a C3–C8 cyclic ring;
$R_3$ is a hydrogen atom or a C1–C10 alkyl group; and
Q is a single bond or a C1–C8 alkylene group.

16. The method of claim 15, wherein the neurotrophic factor is selected from the group consisting of GDNF, BDNF, NGF, NT-3 and combinations thereof.

17. The method of claim 16, wherein the neurotrophic factor is NGF.

18. The method of claim 16, wherein the neurotrophic factor is selected from the group consisting of GDNF, NT-3, BDNF, and combinations thereof.

19. The method of claim 15, wherein Z in the compound of the Formula (I) is $Y_1$:

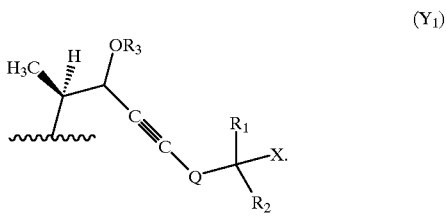

20. The method of claim 15, wherein the compound of Formula (I) is Compound (A):

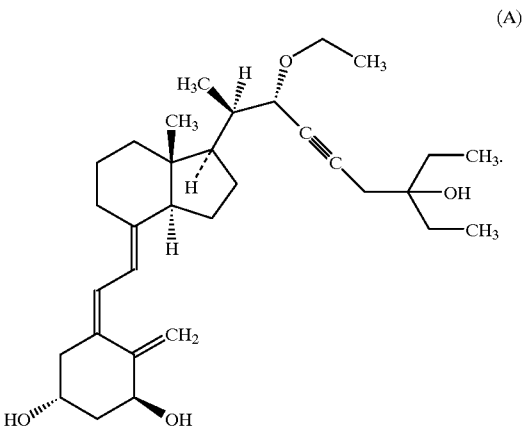

21. The method of claim 15, wherein the compound of Formula I is Compound (B):

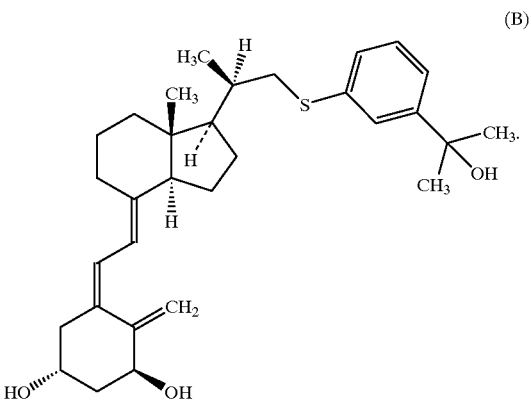

22. The method of claim 15, wherein the compound of Formula I is Compound (C):

(C)

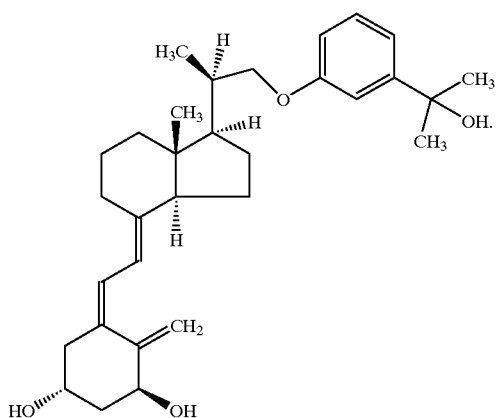

23. The method of claim 15, wherein Z in the compound of Formula (I) is $Y_5$:

($Y_5$)

24. The method of claim 23, wherein the compound of Formula (I) is Compound (E):

(E)

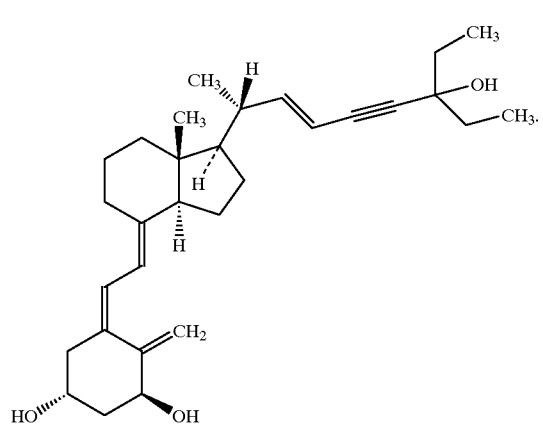

25. The method of claim 15, wherein the compound is administered in an amount of about 0.01 μg to about 10 μg per kilogram body weight.

26. The method of claim 15, wherein $R_1$ or $R_2$ represents a $C_1$–$C_6$ alkyl group substituted with one or more deuterium atoms or fluorine atoms.

27. The method of claim 15, wherein $R_1$ and $R_2$ together with the carbon atom bearing the X group form a $C_3$–$C_8$ ring substituted with one or more deuterium atoms or fluorine atoms.

28. The method of claim 15, wherein $R_3$ is a $C_1$–$C_{10}$ alkyl group substituted with one or more deuterium atoms or fluorine atoms, or $YR_4$, wherein Y is —CO—, —COO—, —COS—, —CS—, —CSO—, —CSS—, —SO— or —$SO_2$— and $R_4$ is a hydrogen atom or a $C_1$–$C_{10}$ alkyl group that is optionally substituted with one or more deuterium atoms or fluorine atoms.

29. The method of claim 15, wherein Q is a $C_1$–$C_8$ alkylene group substituted with one or more deuterium atoms or fluorine atoms.

30. A method of inhibiting the degradation or loss of neural cells comprising administering to a patient a compound of Formula (I):

(I)

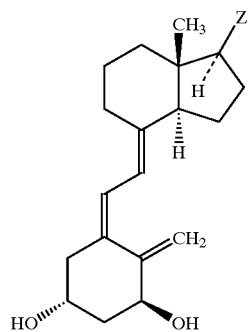

wherein Z is selected from the group consisting of ($Y_1$)

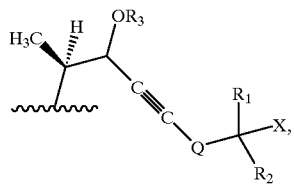

($Y_2$)

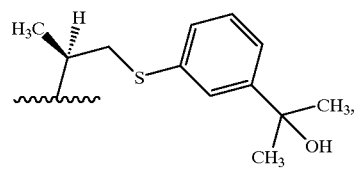

($Y_3$)

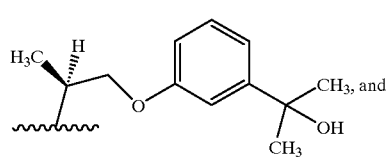

($Y_4$)

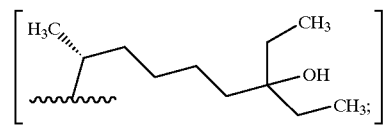

and ($Y_5$)

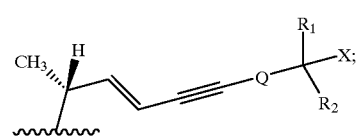

and wherein

X is a hydrogen atom or a hydroxy group;

$R_1$ and $R_2$ each independently represents a hydrogen atom or a C1–C6 alkyl group, or $R_1$ and $R_2$, taken together with the carbon atom bearing the X group, to form a C3–C8 cyclic ring;

$R_3$ is a hydrogen atom or a c1–C10 alkyl group; and

Q is a single bond or a C1–C8 alkylene group.

31. The method of claim 30, wherein Z in the compound of the Formula (I) is $Y_1$:

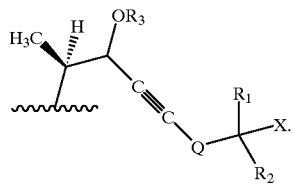

(Y₁)

32. The method of claim 31, wherein the compound of the Formula (I) is Compound (A):

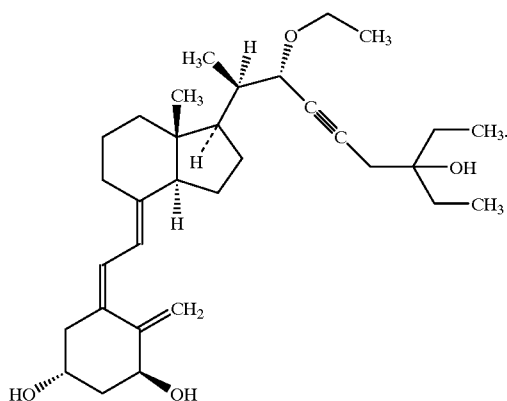

(A)

33. The method of claim 30, wherein the compound of Formula I is Compound (B):

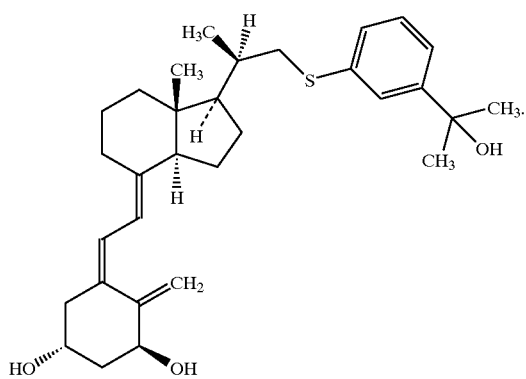

(B)

34. The method of claim 30, wherein the compound of Formula (I) is Compound (C):

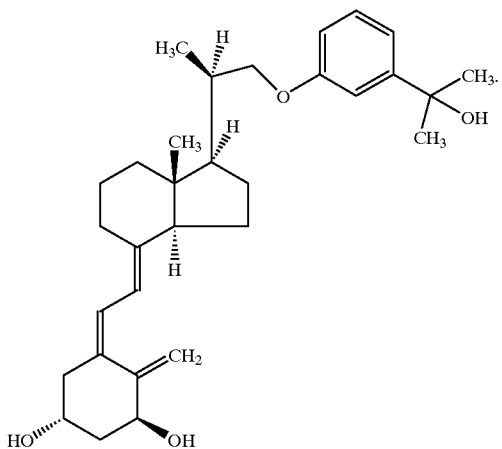

(C)

35. The method of claim 30, wherein Z in the compound of Formula (I) is $Y_5$:

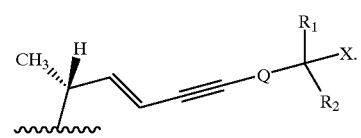

(Y₅)

36. The method of claim 35, wherein the compound of Formula (I) is Compound (E):

(E)

37. The method of claim 30, wherein the compound is administered in an amount of about 0.01 μg to about 10 μg per kilogram body weight.

38. The method of claim 30, wherein $R_1$ or $R_2$ represents a $C_1$–$C_6$ alkyl group substituted with one or more deuterium atoms or fluorine atoms.

39. The method of claim 30, wherein $R_1$ and $R_2$ together with the carbon atom bearing the X group form a $C_3$–$C_8$ ring substituted with one or more deuterium atoms or fluorine atoms.

40. The method of claim 30, wherein $R_3$ is a $C_1$–$C_{10}$ alkyl group substituted with one or more deuterium atoms or fluorine atoms, or YR₄, wherein Y is —CO—, —COO—, —COS—, —CS—, —CSO—, —CSS—, —SO— or —SO₂— and R₄ is a hydrogen atom or a $C_1$–$C_{10}$ alkyl group that is optionally substituted with one or more deuterium atoms or fluorine atoms.

41. The method of claim 30, wherein Q is a $C_1$–$C_8$ alkylene group substituted with one or more deuterium atoms or fluorine atoms.

42. A method of treating multiple sclerosis comprising administering to a patient a compound of Formula (I):

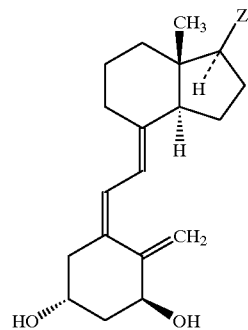

(I)

wherein Z is selected from the group consisting of

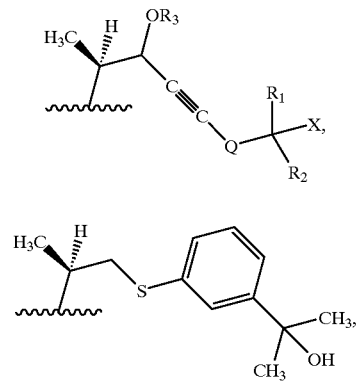

(Y₁)

(Y₂)

(Y₃)

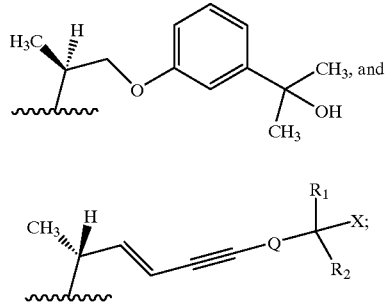

(Y₅)

and
wherein
  X is a hydrogen atom or a hydroxy group;
  R₁ and R₂ each independently represents a hydrogen atom or a $C_1$–$C_6$ alkyl group, or R₁ and R₂, taken together with the carbon atom bearing the X group, form a $C_3$–$C_8$ cyclic ring;
  R₃ is a hydrogen atom or a $C_1$–$C_{10}$ alkyl group; and Q is a single bond or a $C_1$–$C_8$ alkylene group.

43. The method of claim 42, wherein Z in the compound of Formula (I) is Y₁:

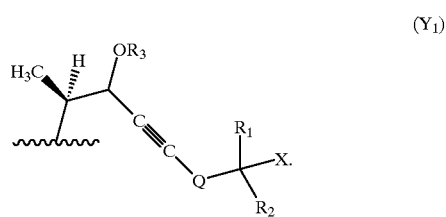

(Y₁)

44. The method of claim 43, wherein the compound of Formula (I) is Compound (A):

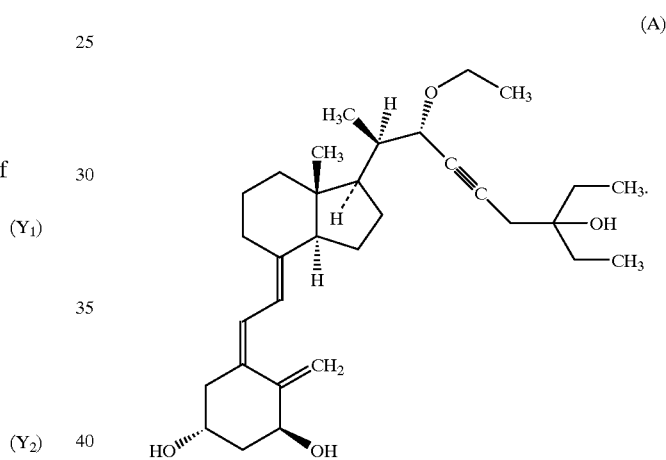

(A)

45. The method of claim 42, wherein the compound of Formula I is Compound (B):

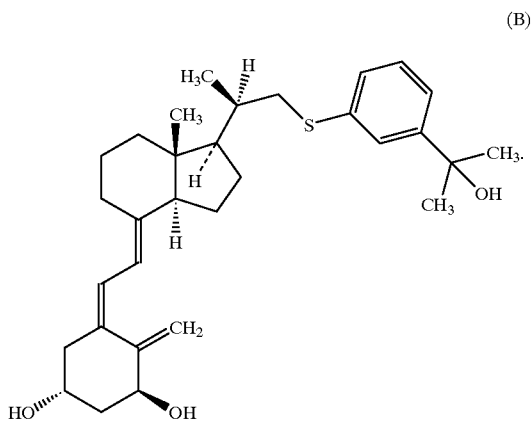

(B)

46. The method of claim 42, wherein the compound of Formula (I) is Compound (C):

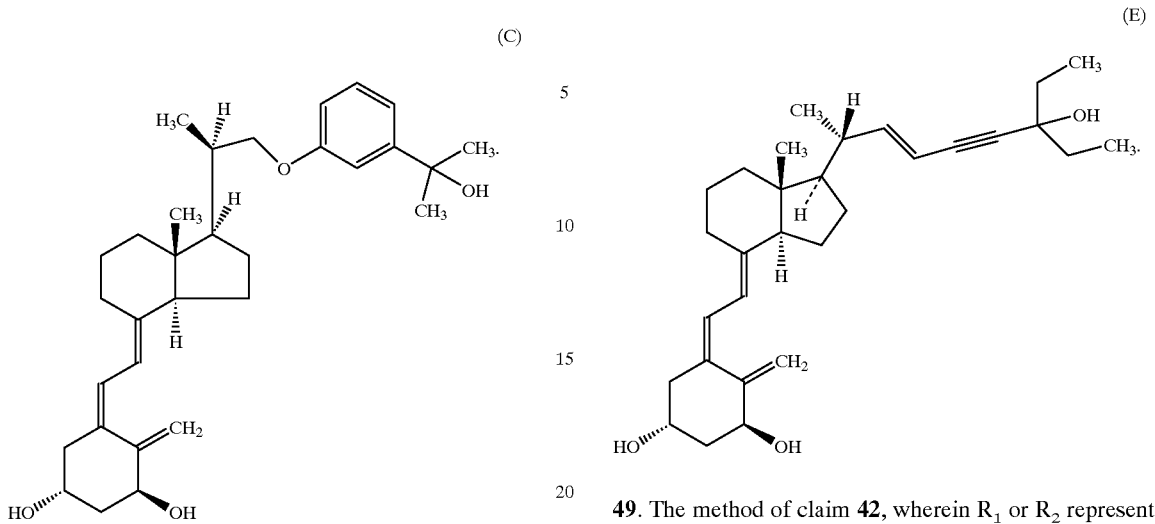

47. The method of claim 42, wherein Z in the compound of Formula (I) is $Y_5$:

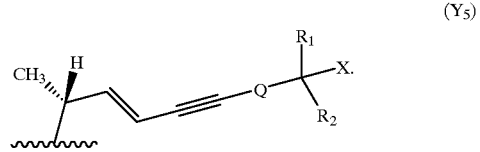

48. The method of claim 47, wherein the compound of Formula (I) is Compound (E):

49. The method of claim 42, wherein $R_1$ or $R_2$ represents a $C_1$–$C_6$ alkyl group substituted with one or more deuterium atoms or fluorine atoms.

50. The method of claim 42, wherein $R_1$ and $R_2$ together with the carbon atom bearing the X group form a $C_3$–$C_8$ ring substituted with one or more deuterium atoms or fluorine atoms.

51. The method of claim 42, wherein $R_3$ is a $C_1$–$C_{10}$ alkyl group substituted with one or more deuterium atoms or fluorine atoms, or $YR_4$, wherein Y is —CO—, —COO—, —COS—, —CS—, —CSO—, —CSS—, —SO— or —SO$_2$— and $R_4$ is a hydrogen atom or a $C_1$–$C_{10}$ alkyl group that is optionally substituted with one or more deuterium atoms or fluorine atoms.

52. The method of claim 42, wherein Q is a $C_1$–$C_8$ alkylene group substituted with one or more deuterium atoms or fluorine atoms.

* * * * *